United States Patent  (10) Patent No.: US 11,965,870 B2
Miresmailli et al.  (45) Date of Patent: *Apr. 23, 2024

(54) MULTI-SENSOR PLATFORM FOR CROP HEALTH MONITORING

(71) Applicant: Ecoation Innovative Solutions Inc., North Vancouver (CA)

(72) Inventors: Saber Miresmailli, North Vancouver (CA); Murray B. Isman, Vancouver (CA); Maryam Antikchi, North Vancouver (CA)

(73) Assignee: Ecoation Innovative Solutions Inc., North Vancouver (CA)

( * ) Notice: Subject to any disclaimer, the term of this patent is extended or adjusted under 35 U.S.C. 154(b) by 0 days.

This patent is subject to a terminal disclaimer.

(21) Appl. No.: 18/054,437

(22) Filed: Nov. 10, 2022

(65) Prior Publication Data

US 2023/0070689 A1 Mar. 9, 2023

Related U.S. Application Data

(63) Continuation of application No. 17/099,422, filed on Nov. 16, 2020, now Pat. No. 11,499,955, which is a
(Continued)

(51) Int. Cl.
*A01G 7/00* (2006.01)
*A01G 13/06* (2006.01)
(Continued)

(52) U.S. Cl.
CPC .......... *G01N 33/0098* (2013.01); *A01G 7/00* (2013.01); *A01G 13/06* (2013.01); *A01G 25/16* (2013.01);
(Continued)

(58) Field of Classification Search
None
See application file for complete search history.

(56) References Cited

U.S. PATENT DOCUMENTS 4,755,942 A 7/1988 Gardner et al.
4,876,647 A 10/1989 Gardner et al.
(Continued)

FOREIGN PATENT DOCUMENTS

CN 108106673 A 6/2018
CN 209181816 U 7/2019
(Continued)

OTHER PUBLICATIONS

Humpston et al., "Data Processing Platform for Analyzing Stereo-Spatio-Temporal Crop Condition Measurements to Support Plant Growth and Health Optimization," U.S. Appl. No. 17/098,172, filed Nov. 13, 2020, 81 pages.
(Continued)

*Primary Examiner* — Paul B Yanchus, III

(57) ABSTRACT

A method includes receiving first sensor data pertaining to plant-related parameters of each of one or more first plants that performed well over time. The method also includes analyzing at least some of the first sensor data to generate a predictive model associated with the one or more first plants. The method further includes receiving second sensor data pertaining to plant-related parameters of each of multiple second plants. In addition, the method includes identifying at least one of the second plants to receive one or more interventions by applying the predictive model to the second sensor data. Identifying the at least one of the second plants includes identifying the at least one of the second plants as having at least one of the plant-related parameters that deviates from at least one of the plant-related parameters of the one or more first plants.

36 Claims, 27 Drawing Sheets

Related U.S. Application Data continuation of application No. 16/268,744, filed on Feb. 6, 2019, now Pat. No. 10,871,480, which is a continuation of application No. 15/219,320, filed on Jul. 26, 2016, now Pat. No. 10,241,097.

(60) Provisional application No. 62/198,761, filed on Jul. 30, 2015.

(51) Int. Cl.
  *A01G 25/16* (2006.01)
  *A01M 21/04* (2006.01)
  *G01D 11/30* (2006.01)
  *G01N 33/00* (2006.01)
  *G05B 15/02* (2006.01)
  *G06N 5/04* (2023.01)
  *G06N 20/00* (2019.01)
  *G08C 17/02* (2006.01)

(52) U.S. Cl.
  CPC .......... *A01M 21/043* (2013.01); *G01D 11/30* (2013.01); *G05B 15/02* (2013.01); *G06N 5/04* (2013.01); *G06N 20/00* (2019.01); *G08C 17/02* (2013.01)

(56) References Cited

U.S. PATENT DOCUMENTS

| | | | |
|---|---|---|---|
| 5,130,545 A | 7/1992 | Lussier | |
| 5,839,106 A | 11/1998 | Bellegarda | |
| 6,397,162 B1 | 5/2002 | Ton | |
| 6,573,512 B1 | 6/2003 | Lucia | |
| 6,657,117 B2 | 12/2003 | Weare et al. | |
| 6,701,665 B1 | 3/2004 | Ton et al. | |
| 7,112,806 B2 | 9/2006 | Lussier | |
| 7,412,330 B2 | 8/2008 | Spicer et al. | |
| 7,487,925 B2 | 2/2009 | Skinner | |
| 7,617,057 B2 | 11/2009 | May et al. | |
| 7,715,013 B2 | 5/2010 | Glaser et al. | |
| 7,987,632 B2 | 8/2011 | May et al. | |
| 8,028,470 B2 | 10/2011 | Anderson | |
| 8,061,080 B2 | 11/2011 | Loebl et al. | |
| 8,249,308 B2 | 8/2012 | Lussier | |
| 8,437,498 B2 | 5/2013 | Malsam | |
| 8,437,879 B2 | 5/2013 | Anderson | |
| 8,476,603 B2 | 7/2013 | Moise et al. | |
| 8,504,234 B2 | 8/2013 | Anderson | |
| 8,836,504 B2 | 9/2014 | Kohler et al. | |
| 9,532,411 B2 | 12/2016 | Conrad et al. | |
| 9,576,786 B2 | 2/2017 | Greenberg et al. | |
| 9,939,132 B2 | 4/2018 | Greenberg et al. | |
| 9,992,991 B2 | 6/2018 | Cink et al. | |
| 10,021,837 B2 | 7/2018 | Greenberg et al. | |
| 10,241,097 B2 | 3/2019 | Miresmailli et al. | |
| 10,339,380 B2 | 7/2019 | Greenberg et al. | |
| 10,627,785 B2 | 4/2020 | King et al. | |
| 10,635,274 B2 | 4/2020 | Greenberg et al. | |
| 10,701,852 B2 | 7/2020 | Calleija et al. | |
| 10,791,037 B2 | 9/2020 | Greenberg et al. | |
| 10,871,480 B2 | 12/2020 | Miresmailli et al. | |
| 10,929,664 B2 | 2/2021 | King | |
| 10,949,974 B2 | 3/2021 | King et al. | |
| 11,003,456 B2 | 5/2021 | King | |
| 11,062,516 B2 | 7/2021 | Greenberg et al. | |
| 2002/0167587 A1 | 11/2002 | Ogasawara | |
| 2002/0170229 A1 | 11/2002 | Ton et al. | |
| 2003/0229497 A1 | 12/2003 | Wilson et al. | |
| 2004/0241635 A1 | 12/2004 | Buckley | |
| 2010/0268562 A1 | 10/2010 | Anderson | |
| 2011/0101239 A1 | 5/2011 | Woodhouse et al. | |
| 2011/0125477 A1* | 5/2011 | Lightner | G05B 13/048 703/11 |
| 2011/0261355 A1 | 10/2011 | Hannel et al. | |
| 2012/0046837 A1 | 2/2012 | Anderson | |
| 2012/0101784 A1 | 4/2012 | Lindores et al. | |
| 2012/0101861 A1 | 4/2012 | Lindores | |
| 2012/0109387 A1 | 5/2012 | Martin et al. | |
| 2012/0114187 A1 | 5/2012 | Duarte | |
| 2012/0150355 A1 | 6/2012 | Anderson | |
| 2013/0197806 A1 | 8/2013 | Belzer et al. | |
| 2014/0012732 A1 | 1/2014 | Lindores | |
| 2014/0035752 A1 | 2/2014 | Johnson | |
| 2014/0059722 A1 | 2/2014 | Krichevsky | |
| 2014/0064568 A1 | 3/2014 | Moon et al. | |
| 2014/0180549 A1 | 6/2014 | Siemens et al. | |
| 2014/0205154 A1 | 7/2014 | De Souza et al. | |
| 2014/0222374 A1 | 8/2014 | Lock et al. | |
| 2015/0027040 A1 | 1/2015 | Redden | |
| 2015/0379721 A1 | 12/2015 | Good et al. | |
| 2016/0223506 A1 | 8/2016 | Shriver et al. | |
| 2017/0030877 A1 | 2/2017 | Miresmailli et al. | |
| 2017/0032258 A1 | 2/2017 | Miresmailli et al. | |
| 2017/0172075 A1 | 6/2017 | Bermudez Rodriguez et al. | |
| 2017/0176595 A1 | 6/2017 | McPeek | |
| 2017/0332544 A1 | 11/2017 | Conrad et al. | |
| 2017/0359943 A1 | 12/2017 | Calleija et al. | |
| 2018/0082362 A1 | 3/2018 | Greenberg et al. | |
| 2018/0082375 A1 | 3/2018 | Greenberg et al. | |
| 2019/0098842 A1 | 4/2019 | Barber, III et al. | |
| 2019/0170718 A1 | 6/2019 | Miresmailli et al. | |
| 2020/0380616 A1 | 12/2020 | King et al. | |
| 2021/0048822 A1 | 2/2021 | Miresmailli | |
| 2021/0072210 A1 | 3/2021 | Miresmailli et al. | |
| 2021/0133443 A1 | 5/2021 | Gurzoni, Jr. et al. | |
| 2021/0298244 A1 | 9/2021 | King et al. | |
| 2021/0302973 A1 | 9/2021 | King et al. | |
| 2021/0304216 A1 | 9/2021 | King et al. | |
| 2021/0304326 A1 | 9/2021 | Greenberg et al. | |
| 2021/0350295 A1 | 11/2021 | Singh et al. | |
| 2022/0130036 A1 | 4/2022 | Gatto et al. | |

FOREIGN PATENT DOCUMENTS

| | | |
|---|---|---|
| CN | 111089829 A | 5/2020 |
| DE | 10148747 A1 | 4/2003 |
| EP | 3491613 A1 | 6/2019 |
| IN | 202041012385 A | 5/2020 |
| JP | 6963102 B2 | 11/2021 |
| WO | 2009141465 A1 | 11/2009 |
| WO | 2018057799 A1 | 3/2018 |
| WO | 2018203337 A1 | 11/2018 |
| WO | 2019134454 A1 | 7/2019 |
| WO | 2019141465 A1 | 7/2019 |
| WO | 2019144231 A1 | 8/2019 |

OTHER PUBLICATIONS

Mohite et al., "RuPS: Rural Participatory Sensing with Rewarding Mechanisms for Crop Monitoring," The 2nd International Workshop on Crowd Assisted Sensing Pervasive Systems and Communications, 2015, 6 pages.
Office Action dated Jul. 23, 2021 in connection with U.S. Appl. No. 15/219,328, 30 pages.
Notice of Allowance dated Dec. 15, 2021 in connection with U.S. Appl. No. 15/219,328, 9 pages.
Office Action dated Jan. 21, 2022 in connection with U.S. Appl. No. 17/099,422, 9 pages.
Jansen et al., "Induced plant volatiles allow sensitive monitoring of plant health status in greenhouses," Plant Signaling Behavior, 824-829, 2009, 6 pages.
Office Action dated Jun. 23, 2023 in connection with U.S. Appl. No. 18/056,610, 15 pages.
Office Action dated Jun. 23, 2023 in connection with U.S. Appl. No. 18/185,211, 9 pages.
Office Action dated Aug. 18, 2021 in connection with Canadian Patent Application No. 2,937,574, 5 pages.
Office Action dated Aug. 19, 2021 in connection with Canadian Patent Application No. 2,937,571, 6 pages.
Office Action dated Jul. 1, 2020 in connection with U.S. Appl. No. 16/268,744, 20 pages.

(56) References Cited

OTHER PUBLICATIONS

Ton et al., "Phytomonitoring: A Bridge from Sensors to Information Technology For Greenhouse Control," Phytech Ltd., 2003, 6 pages.
Office Action dated Sep. 21, 2022 in connection with Canadian Patent Application No. 2,937,571, 6 pages.
Abdullah et al., "Classification of Rubber Tree Leaf Diseases Using Multilayer Perceptron Neural Network," Student Conference on Research and Development (SCORed), Dec. 2007, 6 pages.
Garcia et al., "Digital image processing techniques for detecting, quantifying and classifying plant diseases," Barbedo SpringerPlus, 2013, 12 pages.
Bendig et al., "Combining UAV-based plant height from crop surface models, visible, and near infrared vegetation indices for biomass monitoring in barley," International Journal of Applied Earth Observation and Geoinformation, 2015, 9 pages.
Wijanarko et al., "Development of Mobile RoboVision with Stereo Camera for Automatic Crop Growth Monitoring in Plant Factory," International Conference on Science and Applied Science, AIP Conference Proceeding 2202, 020100-1-020100-7, Dec. 2019, 8 pages.
James, "Assessment of Plant Diseases and Losses," 1974, 22 pages.
Maccines et al., "Visual Classification: Expert Knowledge Guides Machine Learning," IEEE Computer Society, Feb. 2010, 7 pages.
Office Action dated Mar. 16, 2023 in connection with U.S. Appl. No. 17/098,144, 15 pages.
Koppert Biological Systems, "Airbug," Product Specification, Apr. 2020, 3 pages.
Koppert Biological Systems, "Biological pest management to ensure healthy crops," Product List, Dec. 2016, 1 page.
Mandow et al., "The Autonomous Mobile Robot Aurora for Greenhouse Operation," IEEE Robotics and Automation Magazine, Dec. 1996, 11 pages.
Nicolai et al., "Nondestructive measurement of fruit and vegetable quality by means of NIR spectroscopy: A review," Science Direct, Postharvest Biology and Technology 46, 2007, 20 pages.
Ruiz-Altisent et al., "Sensors for product characterization and quality of specialty crops—A review," Computers and Electronics in Agriculture 74, 2010, 19 pages.
Sankaran et al., "A review of advanced techniques for detecting plant diseases," Computer and Electronics in Agriculture, vol. 72, Jun. 2010, 13 pages.
Story et al., "Automated Machine Vision Guided Plant Monitoring System for Greenhouse Crop Diagnostics," ISHS Acta Horticulturae, 1037, 2014, 1 page.
International Search Report and Written Opinion of the International Searching Authority dated Nov. 6, 2020 in connection with International Patent Application No. PCT/CA2020/051099, 11 pages.
Ghaffari et al., "Plant pest and disease diagnosis using electronic nose and support vector machine approach," Journal of Plant Diseases and Protection, 2012, 8 pages.
Office Action dated Mar. 11, 2020 in connection with U.S. Appl. No. 15/219,328, 21 pages.
Final Office Action dated Sep. 18, 2020 in connection with U.S. Appl. No. 15/219,328, 24 pages.
Office Action dated Jan. 6, 2021 in connection with U.S. Appl. No. 15/219,328, 28 pages.
30MHz, "Data should work for the grower (and that means working together)," Oct. 2020, 3 pages.
30MHz, "The Data platform for horticulture—30MHz," Oct. 2020, 13 pages.
30MHz, "Wireless sensors built for horticulture," Sensors, Oct. 2020, 4 pages.
Ecoation, "A Fresh Climate Perspective: What is Stereo-Spatiotemporal Data Collection and Why is it Important," Oct. 2020, 6 pages.
Ecoation, "Our Products / Ecoation Website," Oct. 2020, 14 pages.
Priva, "Priva Sensors for horticulture," Oct. 2020, 5 pages.
SemiosBio Technologies Inc., "We Help Growers Worry Less," Oct. 2020, 8 pages.
Sencrop, "Connected ag-weather: learn more about stations," Oct. 2020, 7 pages.
Fuxman et al., "Real-Time Projections and Estimated Distributions of Agricultural Pests, Diseases, and Biocontrol Agents," U.S. Appl. No. 16/883,354, filed May 26, 2020, 52 pages.
Stewart et al., "Platform for Real-Time Identification and Resolution of Spatial Production Anomalies in Agriculture," U.S. Appl. No. 17/062,381, filed Oct. 2, 2020, 79 pages.
Behmann et al., "A review of advanced machine learning methods for the detection of biotic stress in precision crop protection," Precision Agric, Aug. 2014, 22 pages.
Fuxman et al., "Reduction of Time of Day Variations in Plant-Related Data Measurements," U.S. Appl. No. 17/062,397, filed Oct. 2, 2020, 72 pages.
Stewart et al., "System and Method for Testing Plant Genotype and Phenotype Expressions Under Varying Growing and Environmental Conditions," U.S. Appl. No. 17/062,407, filed Oct. 2, 2020, 75 pages.
Humpston et al., "Stereo-Spatio-Temporal Crop Condition Measurements for Plant Growth and Health Optimization," U.S. Appl. No. 17/098,144, filed Nov. 13, 2020, 80 pages.
Hughes et al., "An open access repository of images on plant health to enable the development of mobile disease diagnostics," 2016, 13 pages.
Humpston et al., "Generation on Stereo-Spatio-Temporal Crop Condition Measurements Based on Human Observations and Height Measurements," U.S. Appl. No. 17/098,193, filed Nov. 13, 2020, 80 pages.
International Search Report and Written Opinion of the International Searching Authority dated Oct. 4, 2021 in connection with International Patent Application No. PCT/CA2021/051041, 9 pages.
International Search Report and Written Opinion of the International Searching Authority dated Nov. 2, 2021 in connection with International Patent Application No. PCT/CA2021/051039, 10 pages.
International Search Report and Written Opinion of the International Searching Authority dated Nov. 1, 2021 in connection with International Patent Application No. PCT/CA2021/051043, 10 pages.
Dong et al., "4D Crop Monitoring: Spatio-Temporal Reconstruction for Agriculture," 2017 IEEE International Conference on Robotics and Automation, IEEE, 2017, 8 pages.
Rumpf et al., "Early detection and classification of plant diseases with Support Vector Machines based on hyperspectral reflectance," Computers and Electronics in Agriculture, 2010, 9 pages.
Dux, "A Speech Recognition System For Data Collection In Precision Agriculture," Purdue University Graduate School Thesis Acceptance, May 2001, 24 pages.
Non-Final Office Action dated Oct. 5, 2023 in connection with U.S. Appl. No. 18/056,604, 16 pages.
Office Action dated Sep. 14, 2023 in connection with U.S. Appl. No. 18/056,598, 13 pages.

\* cited by examiner

MULTI-SENSOR PLATFORM FOR CROP HEALTH MONITORING

CROSS-REFERENCE TO RELATED APPLICATIONS AND PRIORITY CLAIM

This application claims priority under 35 U.S.C. § 120 as a continuation of U.S. patent application Ser. No. 17/099,422 filed on Nov. 16, 2020 (now U.S. Pat. No. 11,499,955), which claims priority under 35 U.S.C. § 120 as a continuation of U.S. patent application Ser. No. 16/268,744 filed on Feb. 6, 2019 (now U.S. Pat. No. 10,871,480), which claims priority under 35 U.S.C. § 120 as a continuation of U.S. patent application Ser. No. 15/219,320 filed on Jul. 26, 2016 (now U.S. Pat. No. 10,241,097), which claims priority under 35 U.S.C. § 119(e) to U.S. Provisional Patent Application No. 62/198,761 filed on Jul. 30, 2015. All of these applications are hereby incorporated by reference in their entirety.

FIELD OF THE INVENTION

The present invention relates to systems and methods for crop monitoring and assessment. Some embodiments relate to multi-sensory devices and platforms for crop monitoring, and methods for operating the same.

BACKGROUND OF THE INVENTION

When food and other crops are grown on a large scale, either in protected cultivation (such as in a greenhouse) or outdoors, growers face several challenges. For example, it is generally difficult for a grower to predict the quality and yield of the crop at a stage in crop development when intervention will still be feasible and useful. Also it can be difficult for a grower to know if, where and when the crop has a problem (such as related to a pest, disease, water, other abiotic stress or nutritional deficit), and the extent of the problem, until it is readily visible to human scouts. Often by that stage it may require expensive and extensive intervention. Crop yield is affected by the physiological performance of the crop throughout its development cycle, which is in turn dependent on external environmental factors among other things. Precise intervention at critical developmental stages, can allow growers to achieve high or optimum yields of the crop. Pest and disease problems are often exacerbated by the large scale on which some crops are grown, the costs for labor, and the speed and ease with which pests and diseases can spread, especially in protected cultivation. When it comes to monitoring crops for pests, diseases and other deleterious conditions, a common approach has been the use of human scouts who visually inspect the crop. However, human scouts whose role it is to locate plants with pests, diseases or other problems, can themselves facilitate the spread of those pests and diseases, for example, through their physical contact with multiple plants and the resulting transfer of pests or diseases from plant to plant. Other limitations of using human scouts for crop monitoring include the speed with which they can cover a large area, and variation in interpretation among individual humans. They also require specific training, and performance of even a diligent employee will be subjective and vary over time.

Many crop management practices are employed prophylactically or simply based on past practices and customs. A common underlying assumption is that crops are uniform and perform evenly which is not necessarily the case, for example, because plants respond to differences in microclimate on a finer scale.

Sensor systems have been developed for crop monitoring, but many of these systems have limitations and shortcomings. For example, some systems use a grid of sensors suspended above the crop (in a zone, usually about an acre in greenhouses) or that fly over the crops. Such sensory grids can be used to monitor environmental conditions or general responses from plants, but generally this is on a course-grained scale. Handheld devices can be used to capture data from individual plants, but these devices tend to be cumbersome to use, and data is captured only from plants that the operator of the handheld device interacts with directly. It is generally not feasible to use a handheld device to capture data from all plants within an area being managed. Often such devices are used by clipping them to the plant or otherwise contacting the plant with the sensing device. Other systems rely on visual detection of causal factors (e.g. pests or disease) by means of motion detection or visual pattern recognition. Visual detection devices can be technologically taxing and economically unfeasible. Additionally, in certain cases, significant damage has already been done to the crop by the time the causal factor is visually identified.

Some sensory devices/systems are geared toward specific indicators (presence of disease, anthocyanin content, emergence of adult pests, etc.) with narrow spectra of responses, often using sensors that function during daylight hours. These technologies are generally large and expensive, and require a human operator, and some of them are time-consuming. For example, fluorescent measurement systems have been used to detect far red spectra produced by plants when exposed to blue or red light. Conventional fluorescent measurement requires complex equipment, and typically a single assessment takes several minutes and sometimes up to about 15 minutes to complete. Other sensory systems can collect very general information (temperature, humidity) that cannot accurately pinpoint problems at the level of individual plants, or at levels of sensitivity that convey timely information in real time.

Expert growers develop a wealth of knowledge and experience by working their crop for multiple years. When currently available, highly automated sensor-based crop monitoring systems are used, the valuable expertise and insight of an experienced grower is no longer effectively harnessed. Furthermore, although humans and existing sensory systems for crop monitoring may, to some degree, be able to identify problems with a crop, they are not capable of predicting the future health of a crop or plant.

SUMMARY OF THE INVENTION

In one aspect, a multi-sensor device for capturing and transmitting sensor data for plants in a crop comprises a housing comprising a plurality of interior cavities and at least one mount on an exterior surface thereof. A plurality of exchangeable sensor modules, occupying the cavities. Each sensor module is for sensing at least one plant-related parameter when the sensor module is positioned proximate to a plant. The housing also contains a control unit operable to control operation of the plurality of sensors, a location tracking system connected to the control unit for tracking the location of the multi-sensor device, and a communications interface connected to the control unit for transmitting and receiving information. The communication interface is operable to transmit data, for example wirelessly, from the plurality of sensor modules. A user-interface is connected to the control unit to allow a user to interact with the device, for example, via a touch screen. The device further includes an electrical power connector for connecting the multi-sensor device to a power source. The electrical power connector can be integral with one or more of the mounts, or can be separate from the mounts.

The housing can be mounted to a handle via the mount for use of the multi-sensor device as a hand-held device. Alternatively the device can be mounted to a mobile platform via the mount. The mobile platform can comprise a propulsion system, a power supply, and a control system for controlling movement of the mobile sensory platform.

In some embodiments of the device, the sensor modules are each coupled to a universal adapter. The universal adapters are connectable to provide power, data and control signal connectivity between one of the sensor modules and the control unit.

The sensor modules can comprise a physiological sensor module, a surface analysis sensor module, and a chemical sensor module. The physiological sensor module can comprise configurable optical probes and tunable detectors. The surface analysis sensor module can comprise a full spectrum light source and spectroscopic detectors. The chemical analysis sensor module can be, for example, a photo-ionization detector, a surface acoustic wave sensor or a quartz crystal microbalance sensor.

The sensor modules can further comprise a thermal imaging sensor module, and/or a vision system module comprising a pair of high resolution RGB-IR cameras for stereo-imaging, and/or a temperature and humidity sensor module.

Each of the plurality of sensor modules is preferably operable to capture data pertaining to at least one plant-related parameter without physical contact with the plant.

In some embodiments of the multi-sensor device, the communications interface is operable to provide two-way communication between the multi-sensor device and a data processing unit over a wireless network, and/or is operable to receive control commands from a wireless mobile device.

In another aspect, a mobile sensory platform for capturing and transmitting sensor data for plants in a crop comprises a propulsion system, and a plurality of sensors mounted to a support structure. Each of the plurality of sensors is for capturing data pertaining to at least one plant-related parameter when the sensor is positioned proximate to a plant. The platform also comprises a communications interface for two-way communication with a data processing unit over a wireless network, an electrical power supply; and a control system for controlling movement of the mobile sensory platform and operation of the plurality of sensors.

Preferably each of the plurality of sensors is operable to capture data pertaining to at least one plant-related parameter without physical contact with the plant.

The plurality of sensors can comprise a physiological sensor and/or a surface analysis sensor and/or a chemical sensor, and optionally microclimate sensors, and/or canopy screening sensors. In some embodiments the sensors of the mobile sensory platform comprise a physiological sensor comprising configurable optical probes and tunable detectors, a surface analysis sensor comprising a full spectrum light source and spectroscopic detectors, and a chemical analysis sensor selected from the group consisting of a photo-ionization detector, a surface acoustic wave sensor and a quartz crystal microbalance sensor.

In some embodiments of the mobile sensory platform the position of at least one of the sensors on the support structure is adjustable during operation of the mobile sensory platform. The control system may be operable to control the position of the at least one of the plurality of sensors.

In some embodiments, the mobile sensory platform of claim further comprises an intervention module for administering remediation to plants in the crop.

The mobile sensory platform can be a ground-based platform or an air-borne platform.

DETAILED DESCRIPTION OF PREFERRED EMBODIMENT(S)

The systems and methods described herein for monitoring and assessing crop health can provide rapid and sensitive screening of individual plant health with reduced human labor, and at a far greater speed than can be accomplished by human scouts. The systems and methods described herein can be deployed outdoors, such as in a field or orchard, or indoors such as in a greenhouse. The systems and methods have an automated component, but are flexible and can be repeatedly modified to enhance the crop-related information that they provide.

Some embodiments also capture and integrate knowledge from human experts into automated crop monitoring systems and methods. Their expertise can be effectively and efficiently captured and applied via an automated system that acts as a proxy, making the technology an extension of the grower.

Furthermore, embodiments of the systems and methods described herein can provide predictive models that can be used to predict future health of plants in a crop based on their current sensor data, so that steps can be taken to try to avoid deterioration in the health of the plant. In some cases a predictive model will provide the capability to identify a potential issue with a plant, before any single sensor or a human expert could detect a problem.

Embodiments of the systems and methods described herein rely primarily on the detection (through sensors) and interpretation (through data analysis) of plant-based signals to provide information about crop health.

Monitoring and assessing crop or plant health as described herein, can include monitoring and assessing performance of the crop or plant. Performance is generally related to the health of the crop or plant.

Automated Crop Monitoring Systems & Methods

Figure 1:
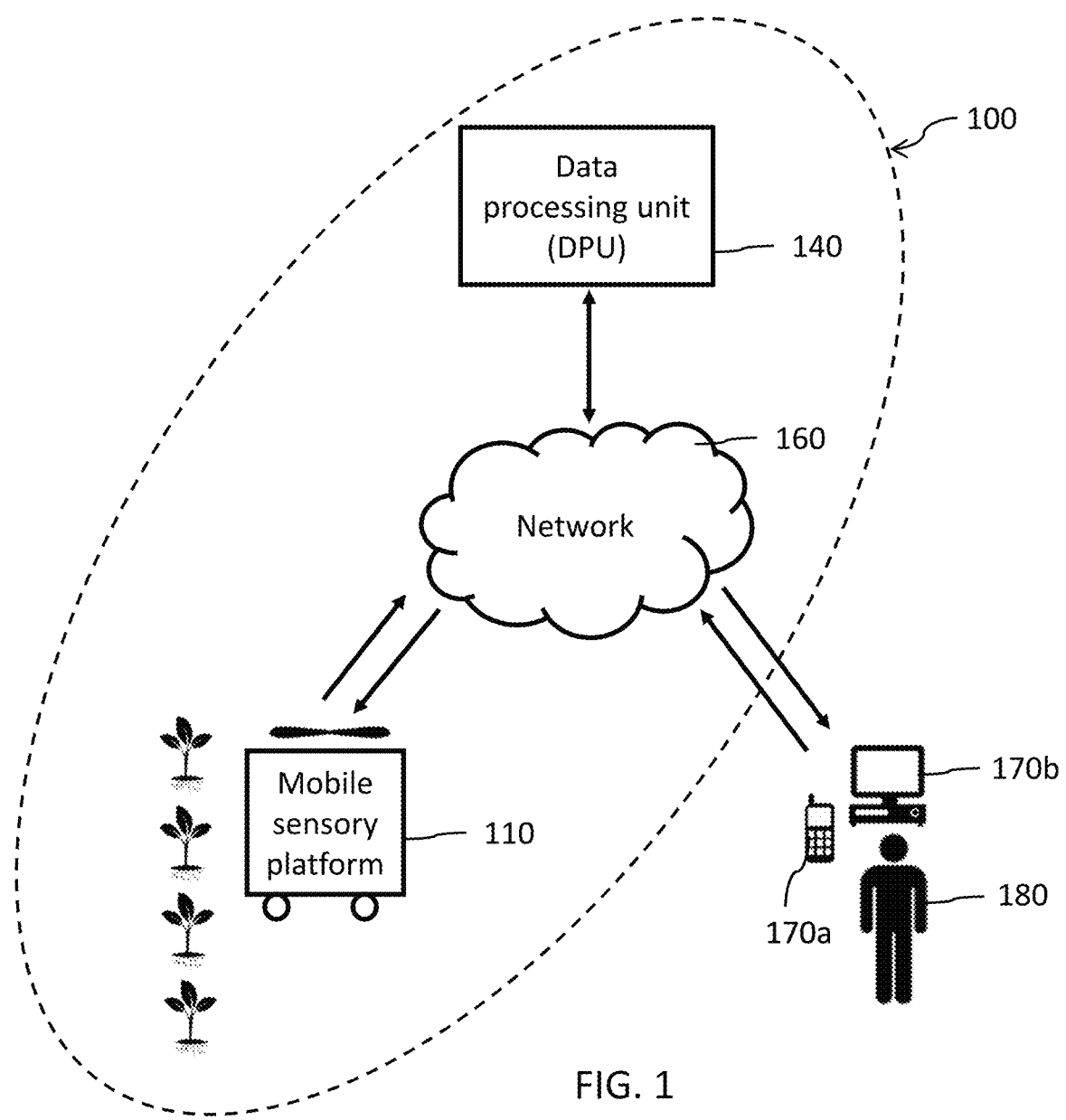
FIG. 1 is a schematic illustration of an embodiment of an automated crop monitoring system comprising a mobile sensory platform.

A first aspect of the technology relates to an automated crop monitoring system and method. An embodiment of such a crop monitoring system 100 is illustrated in FIG. 1. Crop monitoring system 100 comprises a mobile sensory platform 110 comprising a plurality of sensors mounted on a vehicle, cart or drone for example. Mobile sensory platform 110 captures sensor data related to plants in the crop and transmits it to a data processing unit (DPU) 140 via a network 160. In some embodiments, mobile sensory platform 110 comprises more than one mobile sensory platform, and the platforms may communicate and exchange information with one another, as well as with DPU 140. DPU 140 analyzes the sensor data and sends information regarding the crop to an individual 180, such as a grower and or/other parties via one or more end-user devices, such as a smart phone 170a and/or a computer 170b. DPU 140 may also send commands to mobile sensory platform 110. Grower 180 or other parties may also send information to DPU 140 and/or send commands to mobile sensory platform 110 via network 160.

In FIG. 1 arrows are used to indicate transmission of sensor data and/or other information. Preferably system 100 is a web-based and/or cloud-based system, and communication between mobile sensory platform 110, DPU 140, and grower 180 and/or other parties or devices, is primarily or entirely wireless communication.

In some embodiments the mobile sensory platform is designed to operate in the dark, for example, at night. This can be beneficial as it can reduce interference with other greenhouse or field operations. Furthermore, the monitoring system and method may operate with greater sensitivity at night as plants tend to be dormant during periods of darkness. During the daytime, normal practices of staff tending to the crop might temporarily stress the plants, for example moving plant heads, removing shoots, picking fruits, and the like.

In some embodiments the sensors on the mobile sensory platform are proximate to the plant during sensing and data capture, but do not touch the plants or soil. Such non-contact monitoring can help to reduce the spread of pests and diseases.

Preferably the mobile sensory platform is configured to move autonomously among the plants, or in response to commands from a controller, which in some embodiments is a component of the data processing unit.

Figure 2:
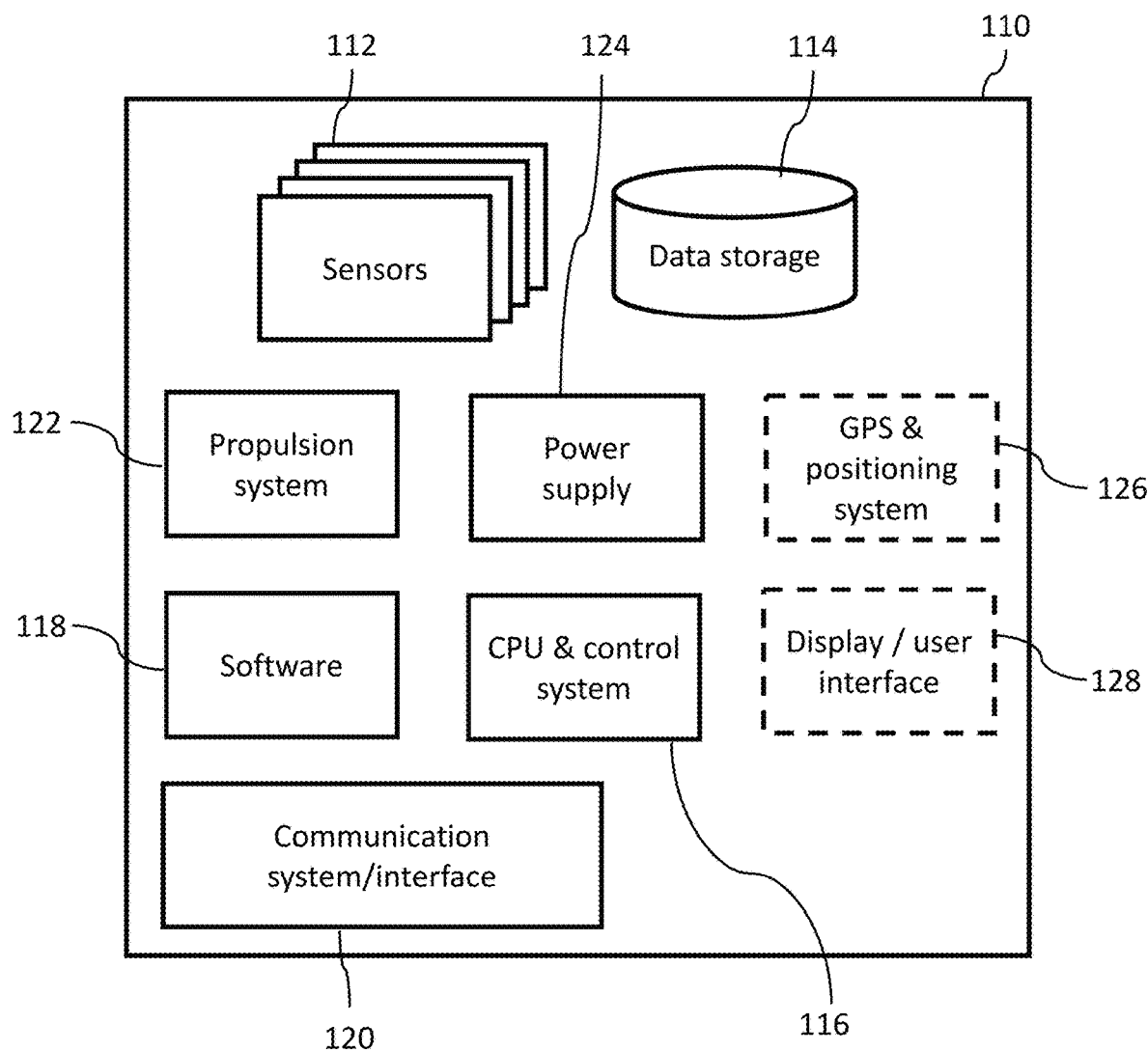
FIG. 2 is a block diagram illustrating components of an embodiment of a mobile sensory platform.

FIG. 2 is a block diagram illustrating components of an embodiment of a mobile sensory platform, such as platform 110 of FIG. 1. Mobile sensory platform 110 comprises a plurality of sensors 112 (as described in further detail below) and a data storage device 114 for storing data captured from sensors 112. Mobile sensory platform 110 also comprises a CPU and control system 116 with associated software 118, and a communications system/interface 120. In some embodiments an external serial connection is provided to allow a user to connect a PC or other device, for example, to modify software on the platform 110. Mobile sensory platform 110 further comprises a propulsion system 122 (for example this could comprise an electric motor, wheels, propellers etc.), a power supply 124 (for example, a battery or other energy storage device and associated recharging equipment and/or a power management system that, in some embodiments, provides a switching between multiple energy sources. Power management system may also incorporate safety and protection devices. Mobile sensory platform 110 may also comprise a GPS and positioning system 126 or similar location tracking system, and a display and/or user interface 128. In some embodiments GPS and positioning system 126 produces and associates a location tag with the sensor measurements; location tags can be stored in data storage device 114 and also transmitted, along with sensor data, via communications system/interface 120. Mobile sensory platform 110 may also comprise an on-board data processing unit, and other components (not shown in FIG. 2).

Figure 3:
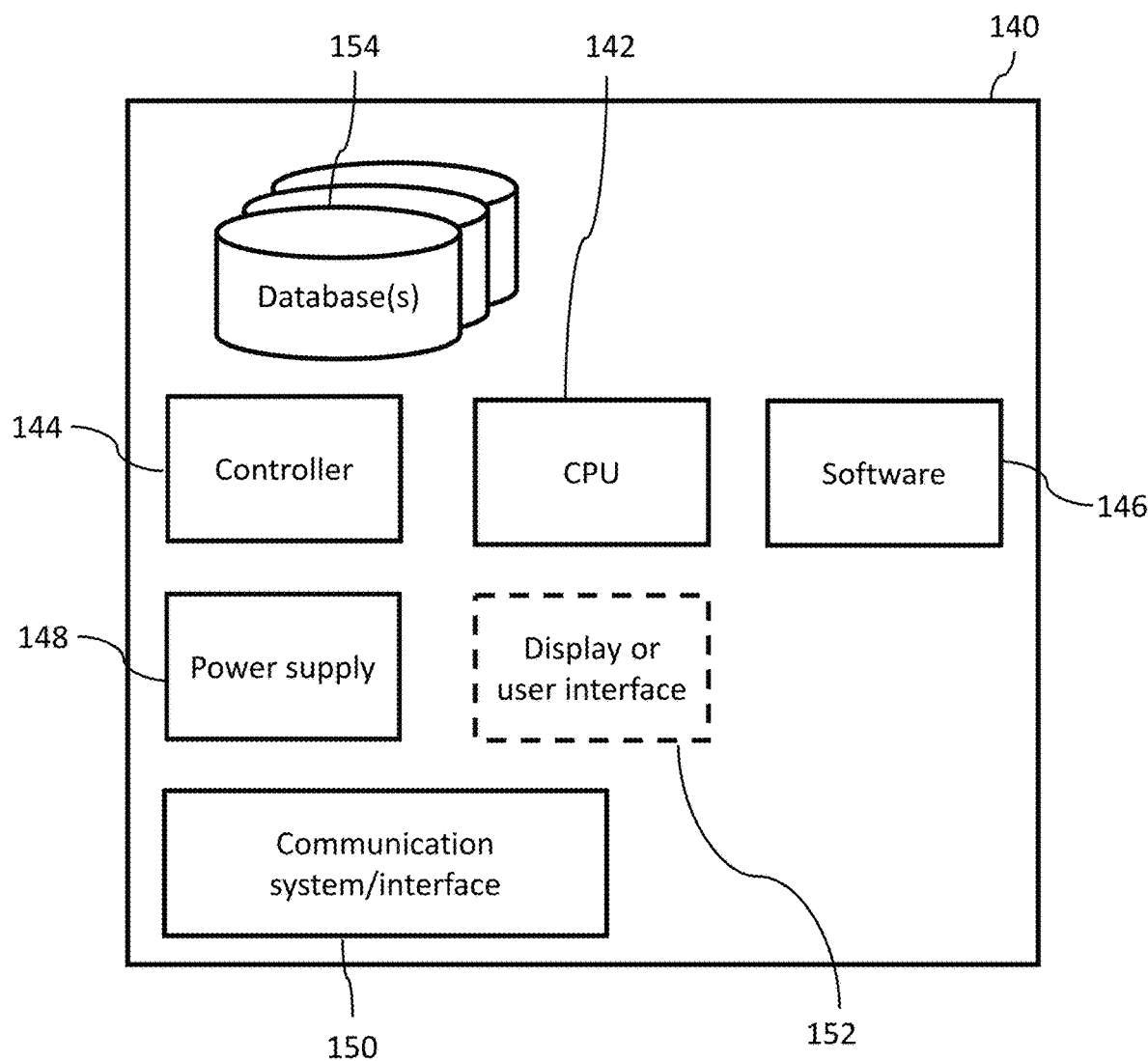
FIG. 3 is a block diagram illustrating components of a data processing unit (DPU).

FIG. 3 is a block diagram illustrating components of a data processing unit (DPU), such as DPU 140 of FIG. 1. DPU 140 comprises at least one CPU 142, a controller 144, software 146, a power supply 148, a communications system/interface 150, and a user interface 152. DPU can also comprise one or more databases 154 for storing raw and/or processed sensor data and/or other information.

Figure 4:
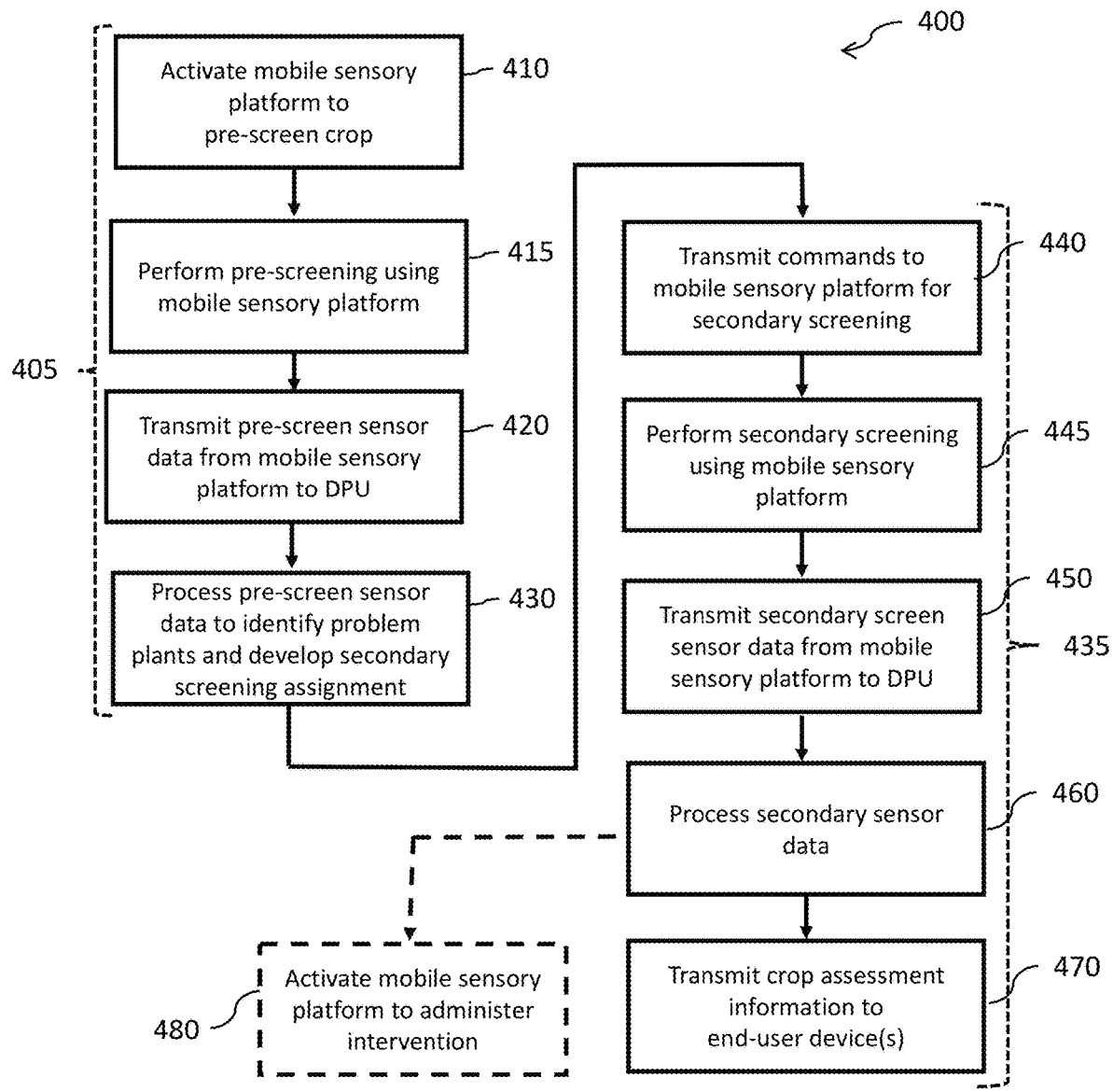
FIG. 4 illustrates an embodiment of a method of operating an automated crop monitoring system, the method involving two phases of data collection and analysis.

One method of operating an automated crop monitoring system, such as system 100 of FIG. 1, is described in reference to FIG. 4 which illustrates a method 400. Method 400 is a two-phase data collection and analysis method. The first phase is a rapid pre-screening phase 405 to identify plants that may have a problem, for example by identifying plants that exhibit a variance based on analysis of their sensor data. In this phase, at 410 data processing system (DPU) 140 activates mobile sensory platform 110 (of FIG. 1) for pre-screening. At 415 mobile sensory platform performs pre-screening, moving between the plants and capturing sensor data relating to some or all of the plants in the crop. Only one sensor or a sub-set of the plurality of sensors 112 is used in pre-screening phase 405. At 420 sensor data from the rapid pre-screening is transmitted from mobile sensory platform 110 via network 160 to DPU 140, where the pre-screening data is processed and analyzed at 430. Plants that may have a problem are identified and tagged for further inspection.

Various known methods can be used to tag the plants or otherwise capture location information, so that the sensor data that is captured for a particular plant can be associated with that plant. In one non-limiting example, each row of crops may be identified using a digital beacon or an RFID tag to signify the beginning of the row. The position of each plant in that particular row can be calculated based on its distance from the beacon or tag.

During 430 DPU 140 develops a secondary screening assignment for mobile sensory platform 110. The secondary screening assignment can be used to gather more detailed information about the crop or specific plants in the crop. The second phase of method 400 is a secondary screening phase 435 which begins at 440. Commands related to the secondary screening assignment are transmitted to mobile sensory platform 110 via network 160. These commands can include commands to activate certain sensors or to cause the mobile sensory platform to move to capture data from particular plants or regions or the crop, and/or the route that should be taken for the secondary screening. Mobile sensory platform 110 performs the secondary screening at 445 in accordance with these commands. For example, during secondary screening 445 mobile sensory platform 110 may move to potential problem plants identified in pre-screening phase 405, and capture further sensor data from those plants using additional ones of the plurality of sensors 112. In some embodiments the particular sensors used in the secondary screening are selected based on the analysis of the pre-screening sensor data captured during the pre-screening phase. Sensor data gathered during the secondary screening phase is transmitted from mobile sensory platform 110 via network 160 to DPU 140 at 450. The sensor data is analyzed at 460 to provide information related to the crop.

In some embodiments of the method, the mobile sensory platform used for secondary screening (for example, at 445) is different from the mobile sensory platform used for pre-screening (for example, at 415). In such one implementation, a multi-sensor device is mounted to a mobility platform such as an all-terrain rover robot with the capability to go to specific areas of a farm or greenhouse. The rover robot carries a drone that is equipped with one or more sensors; for example, these can be a subset of the sensory devices that are on the multi-sensor device that is mounted to the rover robot. During a two-phase mission, the drone flies over a specific area of the crop and performs pre-screening. Once desired pre-screening phase is complete, the drone lands or docks on the rover robot, where it may be re-charged for example. Sensor data from the pre-screening phase may be transmitted from the drone to DPU 140 during the pre-screening phase, or may be transmitted from the drone to DPU 140 (directly or via the rover robot) upon completion of the pre-screening phase. DPU 140 develops a secondary screening assignment for the rover robot, and commands related to the secondary screening assignment are transmitted to the rover robot via network 160 (and optionally via the drone). The rover robot then performs a secondary screening phase, typically in closer proximity to the plants than the drone, and transmits data for analysis by DPU 140 as described above.

Following the sensor data analysis at 460, DPU 140 then transmits information to one or more end-user devices at 470. For example information may be sent to the grower 180 or others via one or more end-user devices, such as smart phone 170a and/or computer 170b. Such information can include, for example: information about the condition of the crop or individual plants, diagnostic information, alerts, action plans, suggested treatments or interventions and the like. In some embodiments, DPU 140 may also send commands to mobile sensory platform 110 to implement one or more interventions in order to attempt to remediate an adverse condition affecting one or more of the plants, as indicated at 480. For example DPU 140 could command mobile sensory platform 110 to disperse a bio-control agent. DPU 140 could also activate other systems at the crop-site to implement one or more interventions in order to try to remediate an adverse condition affecting one or more of the plants. For example, it could activate an irrigation system, adjust a temperature control system or cause nutrients or pesticides to be automatically administered to certain plants.

Events in method 400 can be sequential (with one event being completed before the next begins), or in some cases they can overlap. For example, during the secondary screening phase 435, information relating to one portion of the crop (for which secondary screening sensor data has been captured and analyzed) may be being transmitted from the DPU to the one or more end-user devices at the same time as mobile sensory platform 110 is still capturing sensor data for another portion of the crop. If two different mobile sensory platforms are used for pre-screening and secondary screening (for example, a drone and a rover robot), one platform can be performing pre-screening at the same time the other is performing secondary screening, for example.

There are different approaches that can be used for the analysis of sensor data at 430 and 460.

In one more conventional approach the sensor data is analyzed by using pre-established scientific models and/or comparing the sensor data to known indices or standards. DPU 140 may draw on information stored in other databases for this purpose. For example, particular sensors can be used to look for particular issues with the plants. Data can be collected and compared to a catalogue of plant stress signatures to identify particular problems with the plant or to determine whether the plant is healthy. Some sensors are used to look for specific chemical volatile indicators of a particular pest infestation. Clearly with this approach, it would be necessary to look for many different signatures indicative of many possible stressors. This would typically require use of many different sensors, each geared toward specific indicators (presence of disease, anthocyanin content, emergence of adult pests, etc.) and generally having a narrow spectrum of responses. Such conventional sensors usually function during daylight hours, are generally large and expensive, and require a human operator. Also it can be difficult for conventional sensors to pinpoint specific causal factors in a real crop growing situation where plants are exposed to many potential stressors.

In another approach, rather than analyzing the sensor data to look for specific plant problems or stressors, sensor data is compared to a profile or signature known to be indicative of a healthy plant. In analyzing the sensor data the DPU 140 looks for deviations from this healthy plant profile. This can be done by classifying the sensor data against a set of "trained data" or a model derived therefrom. The trained data can be derived from expert assessments as described in further detail below.

Automated Crop Monitoring Systems and Methods that Capture and Harness Expert Knowledge In this aspect, crop monitoring systems and methods similar to those described above are based upon or enhanced by the utilization of human expertise, for example, from an expert such as an experienced grower, farmer or professional crop advisor assessing the same crop or a similar crop in a similar environment. Embodiments of such systems and methods can capture and integrate this expert knowledge. The expert knowledge is captured from a human expert in a way that allows it to be re-applied later or elsewhere by an automated system and/or used to teach a non-expert.

The system is "trained" based on correlating an assessment of the health of individual plants, as inputted by an expert, with sensor data captured for the same plants. In this context training refers to a process of establishing a repeatable, statistically meaningful relationship between observed data (such as sensor data) and "truth" data—in this case the assessment of an expert—to give "trained data" that can be used as a reference for the classification of new data. This is a form of supervised learning. For example, the trained data can be used in evaluating plant-related sensor data subsequently received from a mobile sensory platform (e.g. in unsupervised learning). Thresholds for different classifications can be established through this process, and data-derived models that can be used for classification and analysis of new data can be developed.

Using this integrated approach, a crop monitoring and assessment system can apply the expert knowledge on an on-going basis during automated monitoring and assessment of the crop, without the need for a human expert to inspect the entire crop. This can make the technology effectively an extension of an expert, such as an experienced grower, farmer or professional crop advisor.

Figure 5:
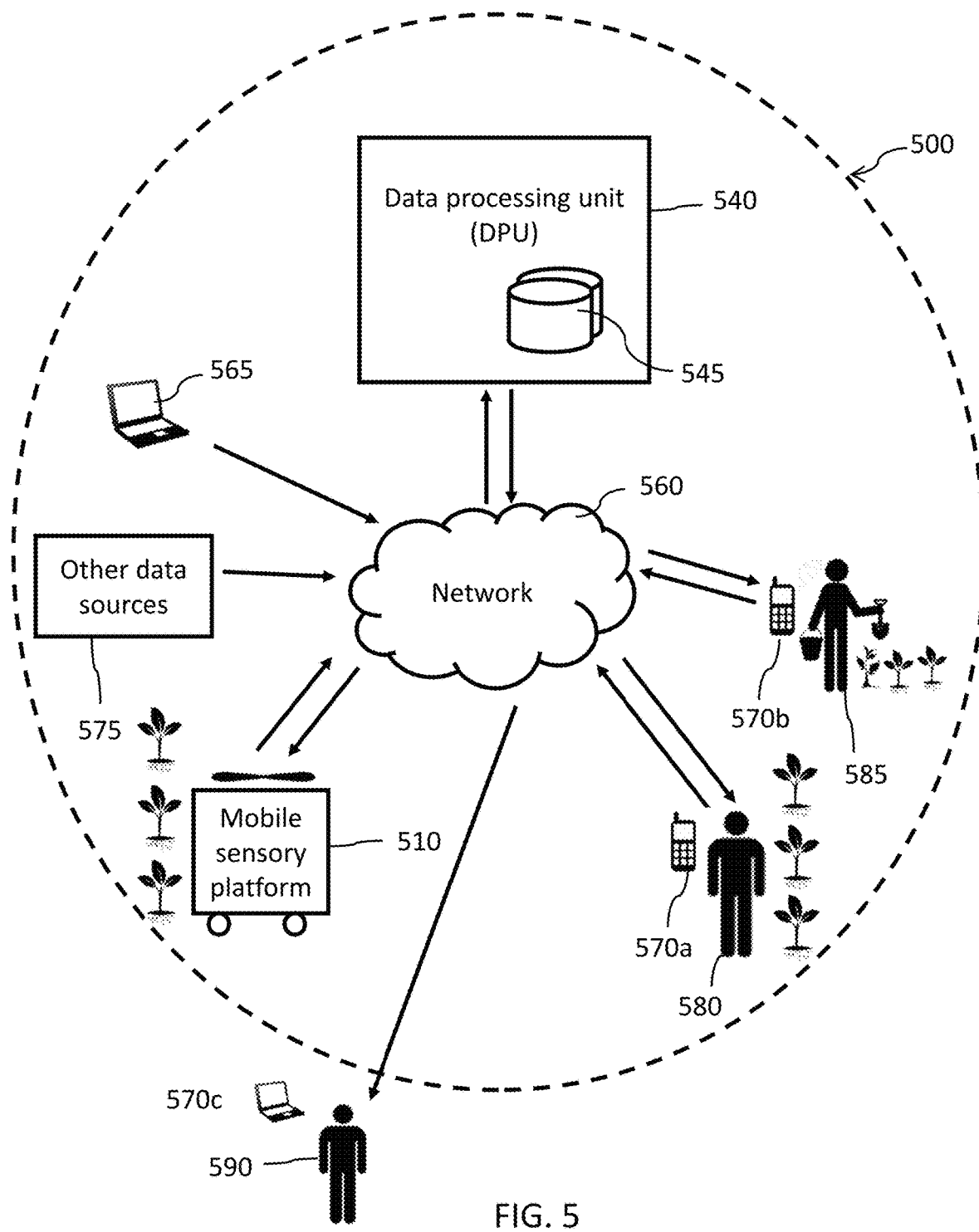
FIG. 5 is a schematic illustration of an embodiment of an automated crop monitoring system that captures and uses expert knowledge and comprises a mobile sensory platform.

An embodiment of a crop monitoring system 500 that captures and uses expert knowledge is illustrated in FIG. 5. In some respects crop monitoring system 500 is similar to crop monitoring system 100 of FIG. 1. System 500 comprises a data processing unit (DPU) 540 that receives data from a plurality of sources via network 560. DPU 540 can be similar to DPU 140 illustrated in FIG. 1 and FIG. 3.

One source of data is a handheld mobile device 570a operated by an expert 580 (such as an experienced grower, farmer or professional crop advisor). Another source of data is a handheld mobile device 570b operated by a non-expert 585. A "non-expert" in this context refers to someone who is not as skilled or experienced as an expert at accurately assessing the health of plants in the crop. For example, it might be a worker who works in the greenhouse attending to the plants (feeding, pruning, harvesting etc.). Handheld mobile devices 570a and 570b comprise a plurality of sensors for capturing sensor data from plants. The handheld devices also provide a way of tagging, locating or identifying the plant associated with the sensor data. Handheld device 570a also allows expert 580 to enter an assessment of plant health. Information and sensor data can be transmitted from handheld devices 570a and 570b to the DPU 540 via network 560. Another source of sensor data is a mobile sensory platform 510 comprising a plurality of sensors mounted on a vehicle, cart or drone for example. Mobile sensory platform 510 can be similar to platform 110 illustrated in FIG. 1 and FIG. 2. Other electronic devices 565 may be used to enter and transmit information and data about the crop to DPU 540 via network 560, for example crop conditions, planting times, source of seeds, environmental factors and the like. Other data sources 575 that can transmit data to DPU 540 via network 560 may include, for example, fixed sensors located around the crop-site.

Software managing the DPU can be based on an open application program interface (API) structure that allows information exchange and integration from and to multiple external data sources. Cross-domain semantic interoperability (CDSI) software allows the DPU to exchange information and commands with other devices and agricultural machines and initiate mutually agreeable tasks.

DPU 540 stores sensor data and information that it receives in one or more databases 545. It also performs data correlation (correlating an assessment of the health of individual plants as inputted by the expert with sensor data captured for the same plants) and stores the resultant "trained data" in one or more databases 545. DPU 540 can then analyze plant-based sensor data using the trained data and/or one or more models derived therefrom, as described in further detail below. In some embodiments, DPU performs more complex analysis of current and historical sensor data, for example, using data mining and machine learning techniques to generate predictive models. In performing data analysis, DPU 540 may supplement the analysis of sensor data using information stored in other databases, such as pre-established scientific models and known indices or standards. DPU 540 can also transmit information regarding the condition of the crop to expert 580, non-expert 585 and or/other parties such as a grower or crop-site manager 590 via one or more end-user devices, such as a smart phones, computers, handheld devices such as 570a, 570b, 570c and other electronic devices. These can be located at the crop-site or remotely. DPU 540 may also send commands to mobile sensory platform 510.

In FIG. 5 arrows are used to indicate transmission of sensor data and/or other information. Preferably the system is a web-based and/or cloud-based system, and communication between mobile sensory platform, data processing unit, and the expert, non-expert and or/other parties or devices, and is primarily or entirely wireless communication System 500 is further described in reference also to FIGS. 6 through 10 which describe a method 600 for crop monitoring and assessment. Method 600 comprises four activities: expert knowledge capture and system training 700, non-expert data acquisition 800, mobile sensory platform data acquisition and analysis 900, and information dissemination 1000. The four activities can, for example, occur repeatedly in series, can be performed in different sequences over time, can overlap, or can occur at least to some extent in parallel.

Figure 6:
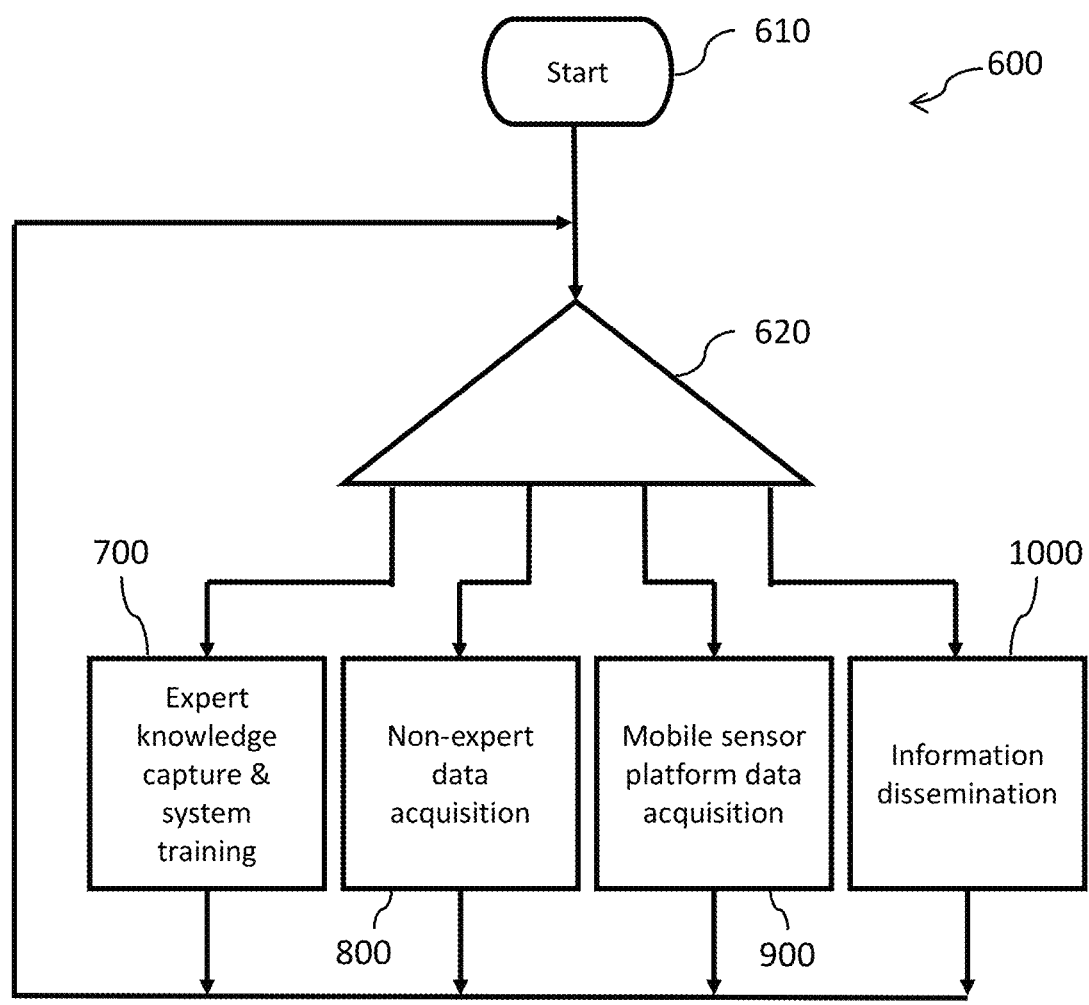
FIG. 6 illustrates an embodiment of a method for crop monitoring and assessment comprising four activities.

Method 600 of FIG. 6 starts at 610, for example, when crop monitoring begins. At 620 method 600 branches into the four activities: expert knowledge capture and system training 700, non-expert data acquisition 800, mobile sensory platform data acquisition and analysis 900, and information dissemination 1000. Each of the activities are described in further detail in the following paragraphs.

Figure 7A:
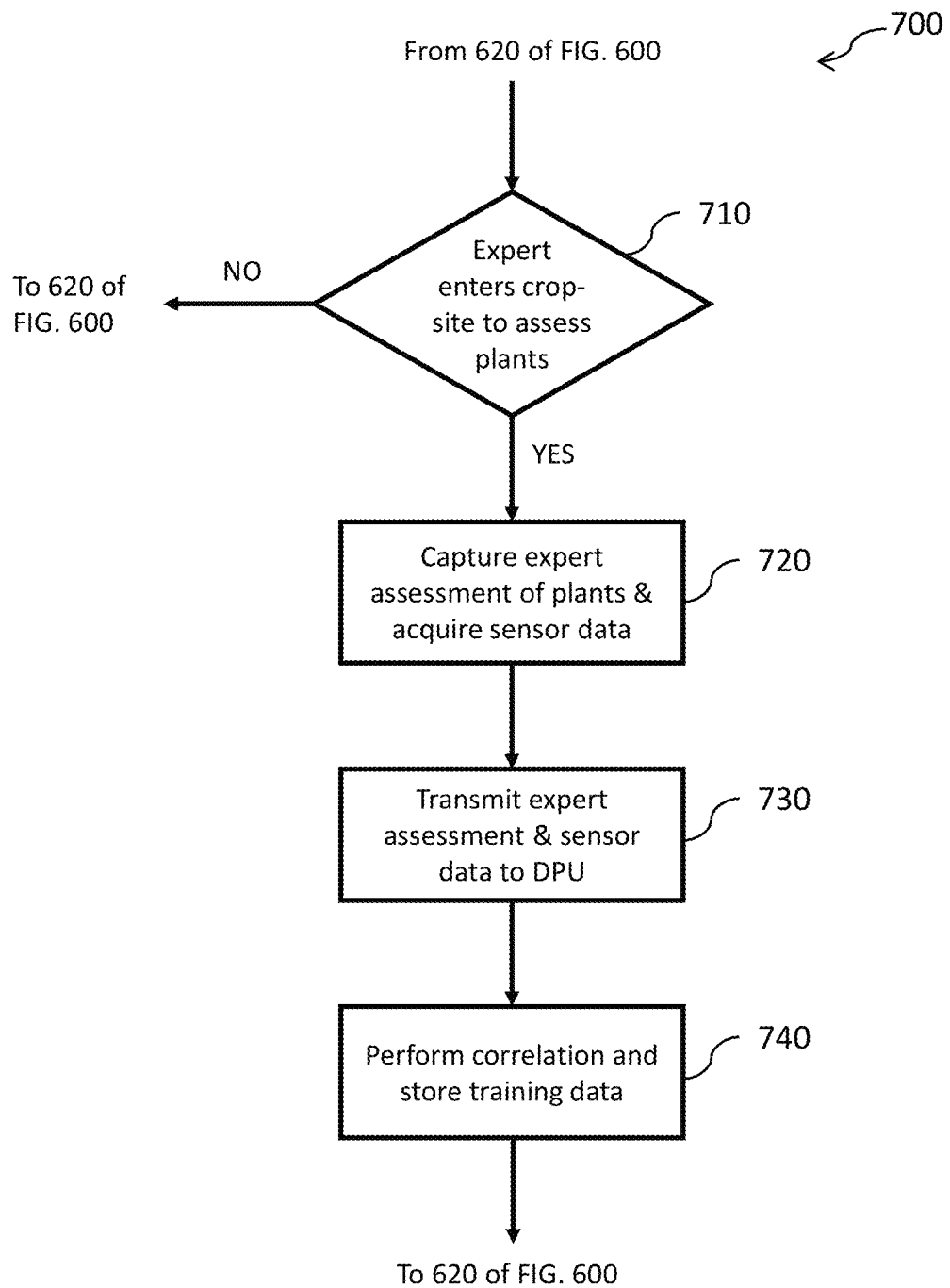
FIG. 7A illustrates an expert knowledge capture and system training activity that is a component of the method illustrated in FIG. 6.

Expert knowledge capture and system training 700 is a fundamental basis of the overall method. As shown in FIG. 7A, activity 700 commences at 710 when an expert enters the crop-site (e.g. field or greenhouse) to assess plants in the crop. At 720 the expert (such as expert 580 of FIG. 5) evaluates individual plants and makes an assessment of their condition or health. The expert also captures sensor data from the plants. Location information or plant tagging information is also captured so that the expert assessment and sensor data can be associated with each particular plant. In some embodiments, the expert can be equipped with a handheld or wearable device (e.g. 570a of FIG. 5) comprising one or more sensors for sensing the plants and capturing and transmitting sensor data via a network (such as 560 shown in FIG. 5) to a data processing unit (such as DPU 540 shown FIG. 5). Preferably the sensors capture plant-based information by sensing characteristics of the plant non-invasively without direct contact with plants. The expert can also input his personal assessment of individual plants using the handheld device, for example, via an app. The assessment can involve a ranking of the plant's condition (e.g. red, orange, green for poor, moderate, healthy respectively), or it can involve a more granular or detailed quantitative or qualitative assessment. The expert repeats the assessment and the capture of sensor data for multiple plants in the crop (although generally this will only be a small fraction of the total crop). At 730 sensor data and expert assessments are transmitted to the DPU. This can be done in real-time plant-by-plant or once the expert has completed that particular visit to the crop. Preferably it is transmitted wirelessly and in real-time.

Activity 700 is typically performed during the day. Multiple experts may perform expert knowledge capture and system training activity 700 simultaneously or at different times for a given crop.

Once the assessments and sensor data are transmitted to the DPU at 730, the raw information (including the plant identifier/locator, and the expert assessment and sensor data for each plant that was evaluated) can be stored. At 740 the DPU correlates the assessments of the health of individual plants (as inputted by the expert) with the sensor data captured for the same plants to generate trained data and, in some cases, one or more data-derived models. The correlation can involve the use of machine learning and classification, and the development of pattern recognition models. The trained data resulting from the correlation is stored. Once there is sufficient trained data to give a reasonable level of accuracy, the trained data, or models derived therefrom, can be used as described in reference to activities 800, 900 and 1000 below. As and when activity 700 is repeated, additional expert assessments and associated sensor data can be added, processed and included in the stored trained data and/or used to further enhance the models. This accumulation of expert knowledge will generally improve the accuracy of the crop monitoring and assessment system over time.

Figure 7B:
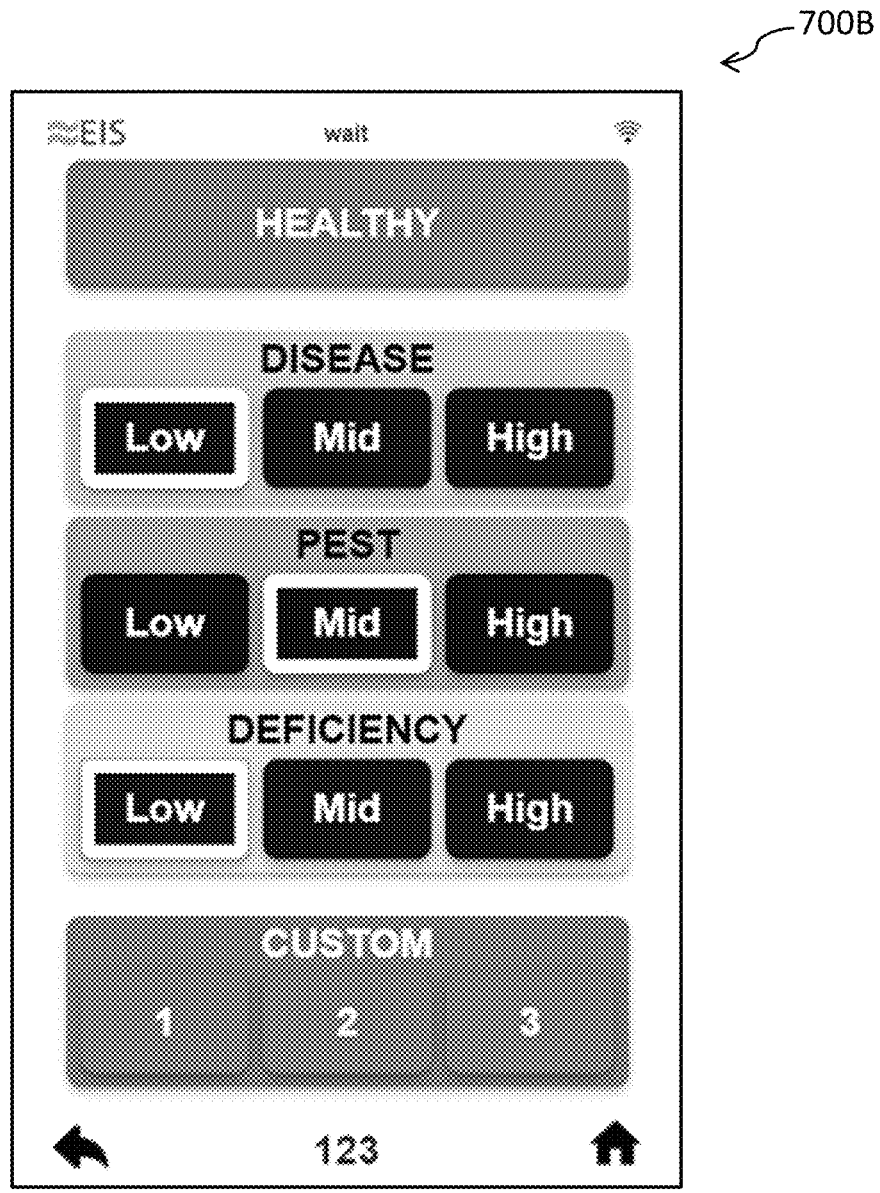
FIG. 7B is a screen-shot from a system training app that can be used by an expert to capture and convey their assessment of plants in a crop.

FIG. 7B shows a screen-shot 700B from a system training app (i.e., a software program or application that can be used on a mobile electronic device, such as a smartphone or tablet) that can be used by an expert to capture and convey to a DPU their assessment of plants in a crop. The expert can assess the plant as healthy or can select the level of different problems; in the illustrated example these are diseases, pests and deficiencies. The custom options allow the expert to assess the plants with respect to other positive or negative attributes of their choosing. For example, the expert may choose a custom profile or feature that they prefer to see in their crop based on their knowledge and experience. This way, growers can create a profile of a healthy plant, an unhealthy plant and/or in some cases, a custom attribute that they want to track. Corresponding sensor data for each plant is also transmitted to the DPU.

In order to quickly build a data-derived model for a particular type of crop and a particular disease or condition, during a training phase an expert may look for plants that are healthy and for plants that are exhibiting a particular problem (e.g. a specific disease or pest) and capture and transmit sensor data along with their expert assessment for just those plants.

Following a training phase that involves supervised learning, for example as described above, unsupervised learning processes can be used to test the resulting data-derived models for accuracy on a new set of unclassified or unlabeled data.

Figure 8:
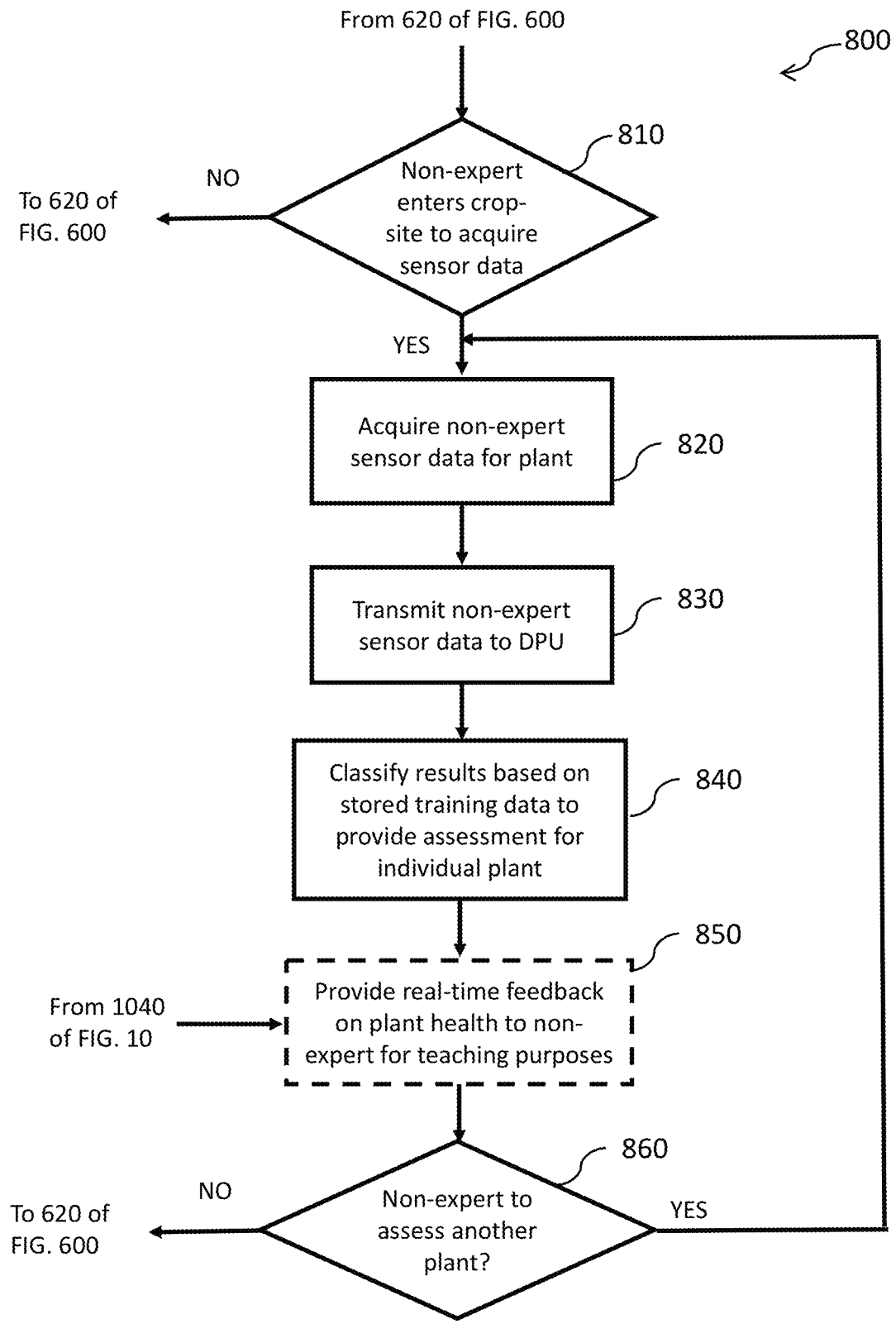
FIG. 8 illustrates a non-expert sensor data acquisition activity that is a component of the method illustrated in FIG. 6.

Non-expert sensor data acquisition activity 800 is illustrated in the flow chart of FIG. 8, and involves the collection of additional plant-based sensor data by a human who is a non-expert. The non-expert is not as skilled or experienced as the expert at accurately assessing the health of plants in the crop. They might be a worker who works in the greenhouse attending to the plants (feeding, pruning, harvesting etc.). Non-expert sensor data acquisition can provide useful data from additional plants in the crop that can be used to develop assignments for automated crop monitoring activities that may happen overnight, for example. It can also be used so that the non-expert can learn how to assess plant health "like an expert"—this learning aspect is described in further detail below. Non-expert sensor data acquisition activity 800 may be performed on a daily basis, frequently or not at all, as part of overall method 600.

Referring to FIG. 8, activity 800 commences at 810 when a non-expert enters the crop-site to capture sensor data for plants in the crop. At 820 the non-expert (such as non-expert 585 of FIG. 5) captures sensor data for a plant, along with location information or plant tagging information so that sensor data can be associated with the particular plant. In some embodiments, the non-expert is equipped with a handheld or wearable device (e.g. 570b of FIG. 5) comprising one or more sensors for sensing plants and capturing and transmitting sensor data to a data processing unit (such as DPU 540 shown FIG. 5). For example, the handheld sensor device can be similar to or the same as the one used by the expert in activity 700. Sensor data capture may happen passively as the non-expert moves from plant to plant performing other tasks, or may require the non-expert to activate the sensors and capture sensor data, for example, by pressing a button. At 830 sensor data is transmitted to the DPU. This can be done in real-time plant-by-plant (as shown in FIG. 8), or for multiple plants once the non-expert has completed that particular visit to the crop. Preferably it is transmitted wirelessly and in real-time.

Activity 800 is also typically performed during the day. Multiple non-experts may be performing sensor data acquisition activity simultaneously or at different times for a given crop. For example, a large crew of workers could be equipped with handheld or wearable sensor devices in order to capture plant-based sensor information while they are busy performing other tasks related to the crop.

Once sensor data is transmitted to the DPU at 830, the raw information (including plant identifier/locator and sensor data for each plant that was evaluated) can be stored. At 840 the DPU classifies the condition of each plant by passing the sensor data through a model derived from the trained data (generated from expert knowledge capture and system training activity 700). Plant health information based on this classification can be disseminated for various purposes as described below in reference to activity 1000 of FIG. 10A. In some embodiments, such as at 1040 of FIG. 10A, information is sent back to the non-expert. For example, referring again to FIG. 8, handheld sensor data captured by the non-expert for each plant is analyzed in real-time by the DPU and, at 850, the non-expert may receive an immediate assessment of the condition of the plant from DPU 540 via their handheld device 570b. For example, this could be a simple ranking of the plant's condition (e.g. red, orange, green for poor, moderate, healthy respectively). The real-time assessment delivered to the non-expert is based on a model derived from trained data that was derived from expert assessments in activity 700. In this way the non-expert can inspect the plant and learn how it would have been assessed by an expert, without the expert needing to be present to teach the non-expert. Once the non-expert has received feedback on a particular plant at 850 they can move on to another plant at 860 if desired.

Figure 9:
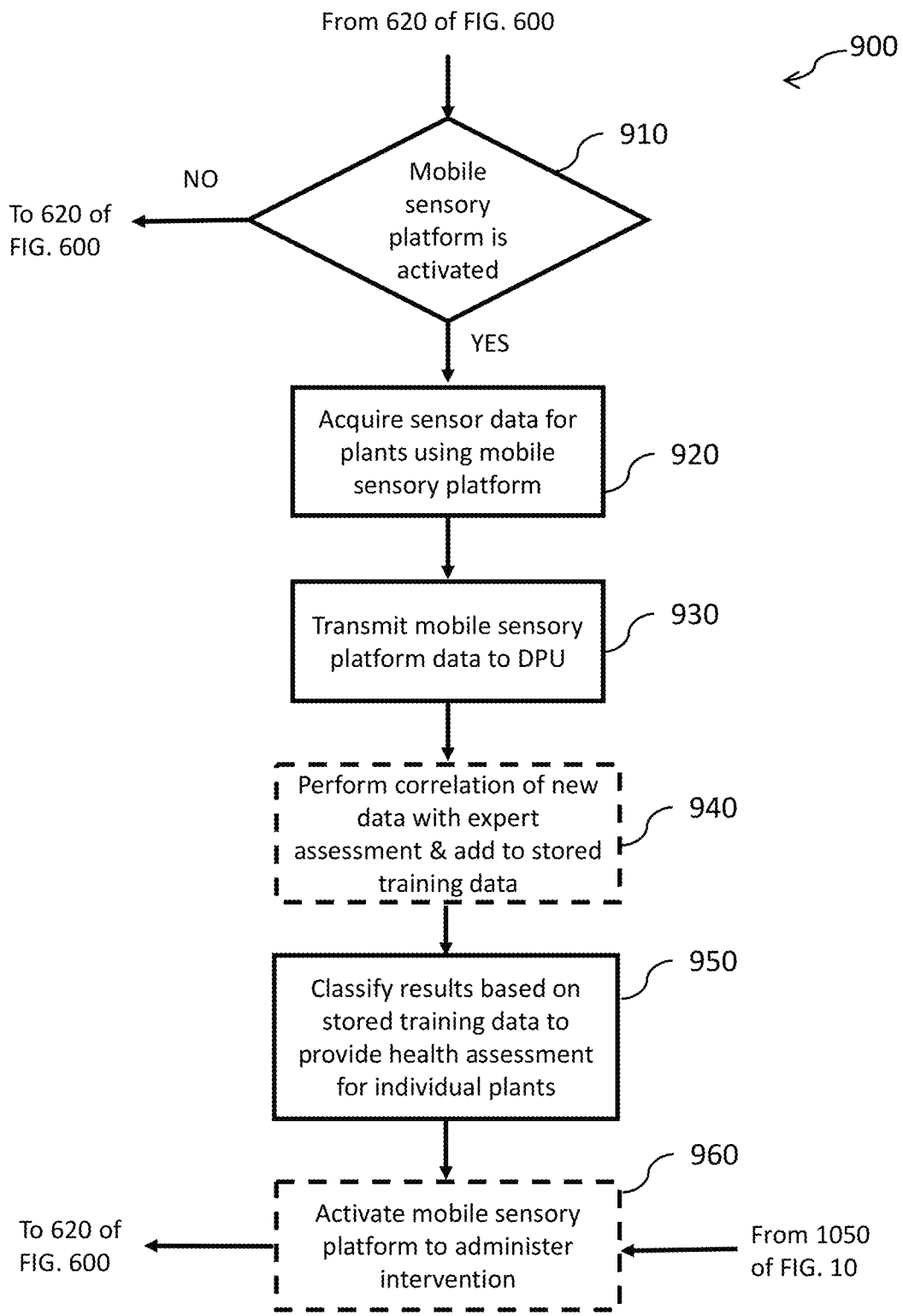
FIG. 9 illustrates a mobile sensory platform data acquisition and analysis activity that is a component of the method illustrated in FIG. 6.

Mobile sensory platform data acquisition and analysis activity 900 is illustrated in the flow chart of FIG. 9, and is an important aspect of method 600. This activity can be performed during the day, or at night when there might be reduced interference with other greenhouse or field operations. At night the sensing may be more sensitive to the presence of disease or pests, as plants tend to be dormant and less stressed by other external factors during periods of darkness. Multiple mobile sensory platforms may be used simultaneously to cover different regions of the crop, for example, to allow the whole crop to be assessed in a shorter time-frame.

Activity 900 starts when a mobile sensory platform (such as mobile sensory platform 510 of FIG. 5) is activated to move between the plants and capture data relating to some or all of the plants in the crop. The mobile sensory platform may have a different number of sensors than the handheld devices used by the expert and non-expert in activities 700 and 800. In some cases, it will have a greater number of sensors, but not always. Also, it may have a different set of sensors usually, but not always, with some sensor types in common with the handheld devices.

The mobile sensory platform can be operated, for example, in a similar manner to that described in reference to FIG. 4, with a pre-screening phase and a more detailed secondary screening phase. In other embodiments mobile sensory platform can be operated with a single-pass screening operation.

With these, or other methods of operating the mobile sensory platform, sensor data is captured at 920. Location information or plant tagging information is also captured at 920, so that sensor data can be associated with each particular plant. At 930 data is transmitted to the DPU. The sensor data from the mobile sensory platform can be transmitted to the DPU in real-time or once a portion or all of the screening session is completed. Preferably it is transmitted wirelessly.

Once sensor data from the mobile platform is transmitted to the DPU at 930, the raw information (including plant identifier/locator and sensor data for each plant that was evaluated) can be stored. In some embodiments, further correlation can be performed at 940 to generate additional trained data and/or to enhance data-derived models. For example if data has been captured from sensor-types on the mobile sensory platform that are not on the handheld devices, this data may be correlated with the expert assessments obtained for the same plants during activity 700 to provide further trained data and/or enhance models that can be stored and used for classification of plant health. At 950 the DPU classifies the condition of each plant by applying a model, derived from the trained data, to the sensor data received from mobile sensory platform at 930. Plant health information based on this classification can be disseminated for various purposes as described below in reference to activity 1000 of FIG. 10A. In some embodiments, such as at 1050 of FIG. 10A, commands are sent to the mobile sensory platform based on the analysis of sensor data received from the mobile sensory platform. For example, at 960 (see FIG. 9), commands are transmitted to the mobile sensory platform to cause it to implement one or more interventions in order to attempt to remediate an adverse condition affecting one or more of the plants, for example, at 960 DPU 540 could command mobile sensory platform 510 to disperse a bio-control agent.

Figure 10A:
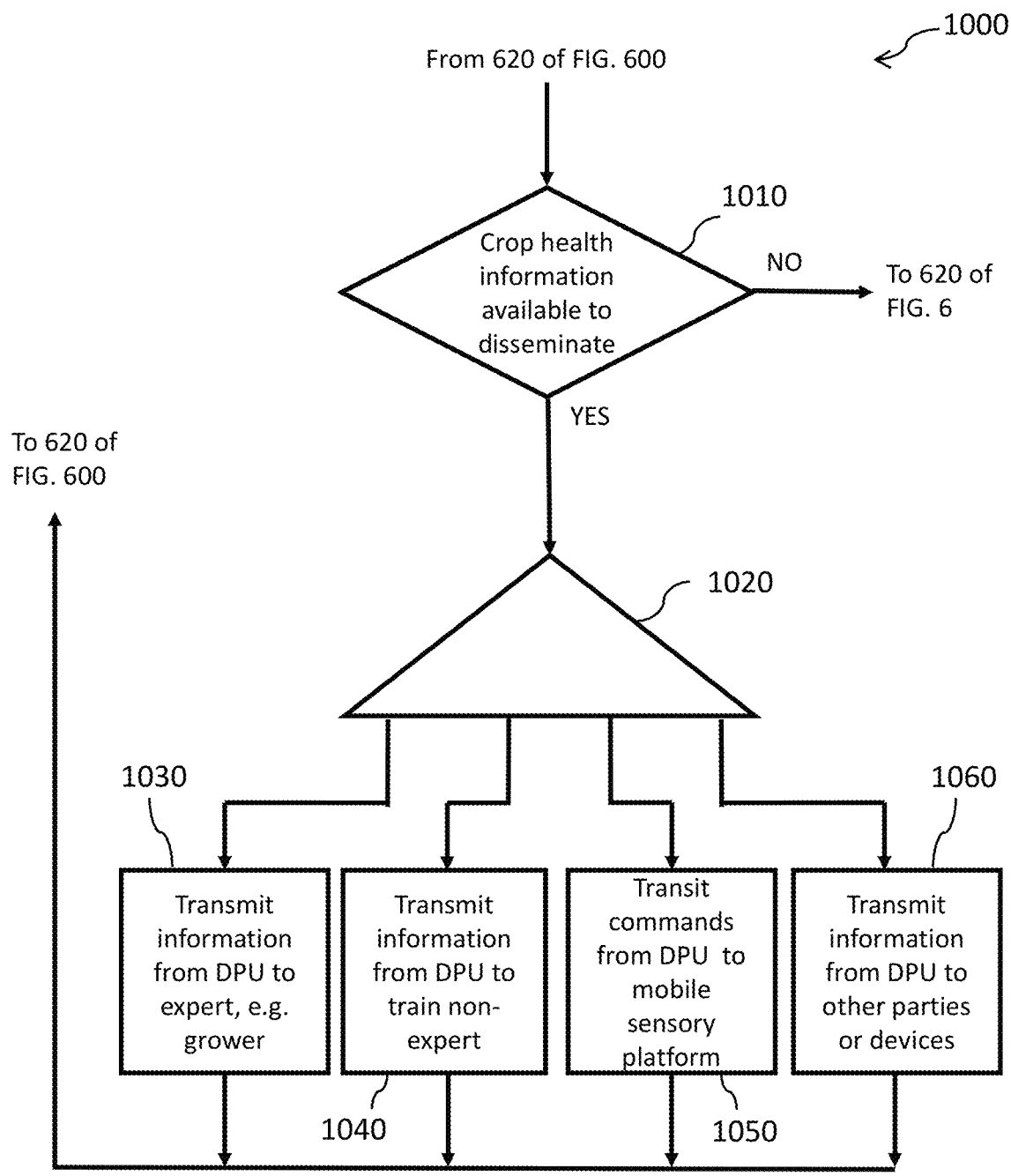
FIG. 10A illustrates an information dissemination activity that is a component of the method illustrated in FIG. 6.

Information dissemination activity 1000 is illustrated in FIG. 10A which shows some non-limiting examples of how information can be delivered and used. Activity 1000 starts at 1010, for example, when there is updated information about the crop available to disseminate or when an end-user desires or requests information. At 1020 activity 1000 branches into the four exemplary information dissemination activities which can occur asynchronously. For example, these can each occur repeatedly, can occur at different times, or can overlap, or occur simultaneously.

At 1030 information about the crop is transmitted to an expert, such as grower 580 in FIG. 5. This information could be delivered each morning, for example, based on analysis and classification of sensor data captured overnight for the entire crop by mobile sensory platform 510 performing activity 900. Or it could be delivered in real-time as the DPU analyzes data received from the mobile sensory platform in real-time. For example, DPU could provide a grower with an alert, an alert plus a diagnosis of the problem, or an alert plus a diagnosis plus a suggested intervention plan, for specific plants or regions of the crop that are not healthy. In a non-limiting example of an implementation of the information delivery, a grower might use an interactive map of a farm or greenhouse where problematic areas identified by the DPU are marked by dots on the map. Once the grower clicks on each dot, specific information about the type or severity of the issue at that location may be displayed, along with a suggested intervention plan. In yet another non-limiting example, the information delivery will be done via a wearable device, which can be used by growers, experts and/or non-experts. The DPU may generate a notification, for example, in the form of an audible alarm or a haptic vibration that occurs when the wearer of the device comes in close proximity to a problematic area. The intervention plan may be communicated as part of the notification.

At 1040 information about the crop is transmitted to a non-expert, such as 585 in FIG. 5. For example, this information could be delivered to a worker each morning to guide the worker to specific areas of the crop that need intervention based on analysis and classification of sensor data gathered overnight for the entire crop by mobile sensory platform 510 performing activity 900. This could allow the worker to apply interventions only to those specific areas, as opposed to general broad-based applications, thereby reducing costs and exposure risk. In other example, information is delivered in real-time to a non-expert performing activity 800 of FIG. 8 so that the non-expert can learn on a plant-by-plant basis how an expert would assess plant health. This is described above in reference to 850 of FIG. 8.

At 1050 information and/or commands are transmitted to a mobile sensory platform (such as platform 510 of FIG. 5) based on analysis and classification of sensor data received from the mobile sensory platform. For example, these could be further screening assignments or commands to perform interventions based on analysis and classification of sensor data received from the mobile sensory platform. The latter is described in more detail above in reference to 960 of FIG. 9.

At 1060 information about the crop is transmitted to other parties or devices either at the crop-site or at other locations.

In the above examples, during information dissemination activities 1030, 1040, 1050 and 1060, information can be pushed from the DPU or can be pulled upon request by the end-user or device.

Figure 10B:
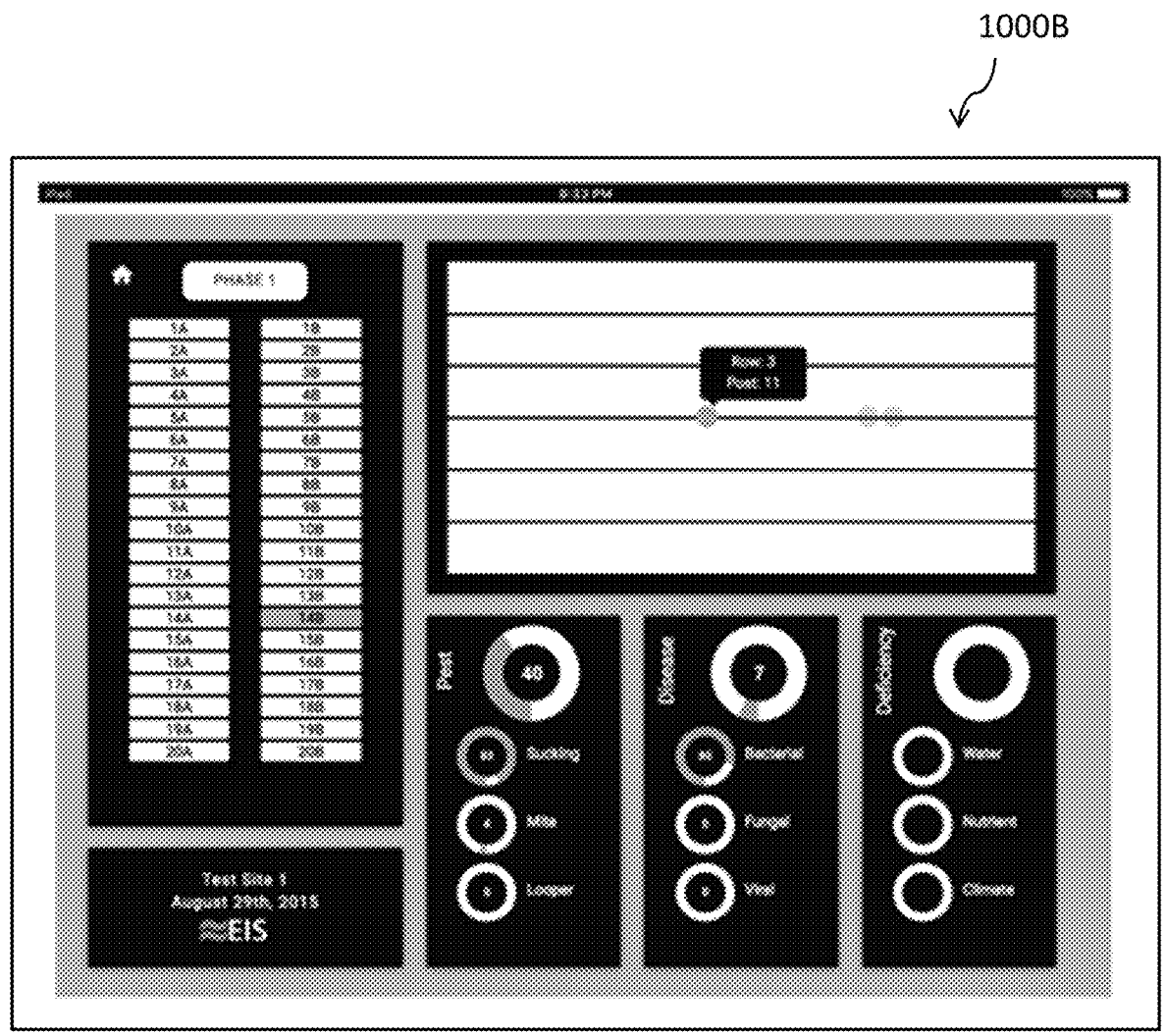
FIG. 10B is a screen-shot from a reporting app that can be used to convey information relating to crop health to a person, such as a grower.

FIG. 10B shows a screen-shot 1000B from a reporting app that can be used to convey information about the crop to a person, such as a grower. During a setup process, the growers may define number of phases they have in their greenhouses and number of bays in each phase as well as the number of rows in each bay, thereby creating a map of the greenhouse. The dynamic mapping panel on the left alerts users to the location of problems in their crops—it indicates the phase and bay of the greenhouse for which information is being reported. In the top right quadrant the rows of that particular bay are shown. The dots indicate plants identified by the system as deviating from a healthy profile. The user can click on a dot and the location of the plant is more precisely identified, and a description of the problem and an indication of the probability of the problem is displayed, as shown in the lower right quadrant. In the illustrated example, a plant at post 11, in row 3 of bay 14B in phase 1 of the greenhouse is indicated as having a high probability that it is suffering from a sucking pest infestation and a lower probability that the problem is a bacterial disease.

Using the approach described above, the knowledge of an expert can be captured and then extended and applied at future times and/or at other locations without the expert being physically present at those times or in those locations. It is extremely valuable to be able to harness an expert's knowledge and experience in this way, both for teaching other people how to assess crops and for actual crop assessment. For example, sensor data from similar crops in other (remote) locations can be captured via mobile sensory platforms and/or handheld devices and then one or more data-derived models in the DPU can be applied to the sensor data to provide crop health assessment information about that crop without an expert needing to be there at all.

Another advantage of the present approach is that the machine-based analysis of the data by the DPU will provide a more consistent and accurate assessment of plants than a human. Generally, even an expert will not always provide a consistent assessment through the day or from one day to the next, due to a variety of factors such as fatigue, distractions or challenging environmental conditions, for example.

Figure 11:
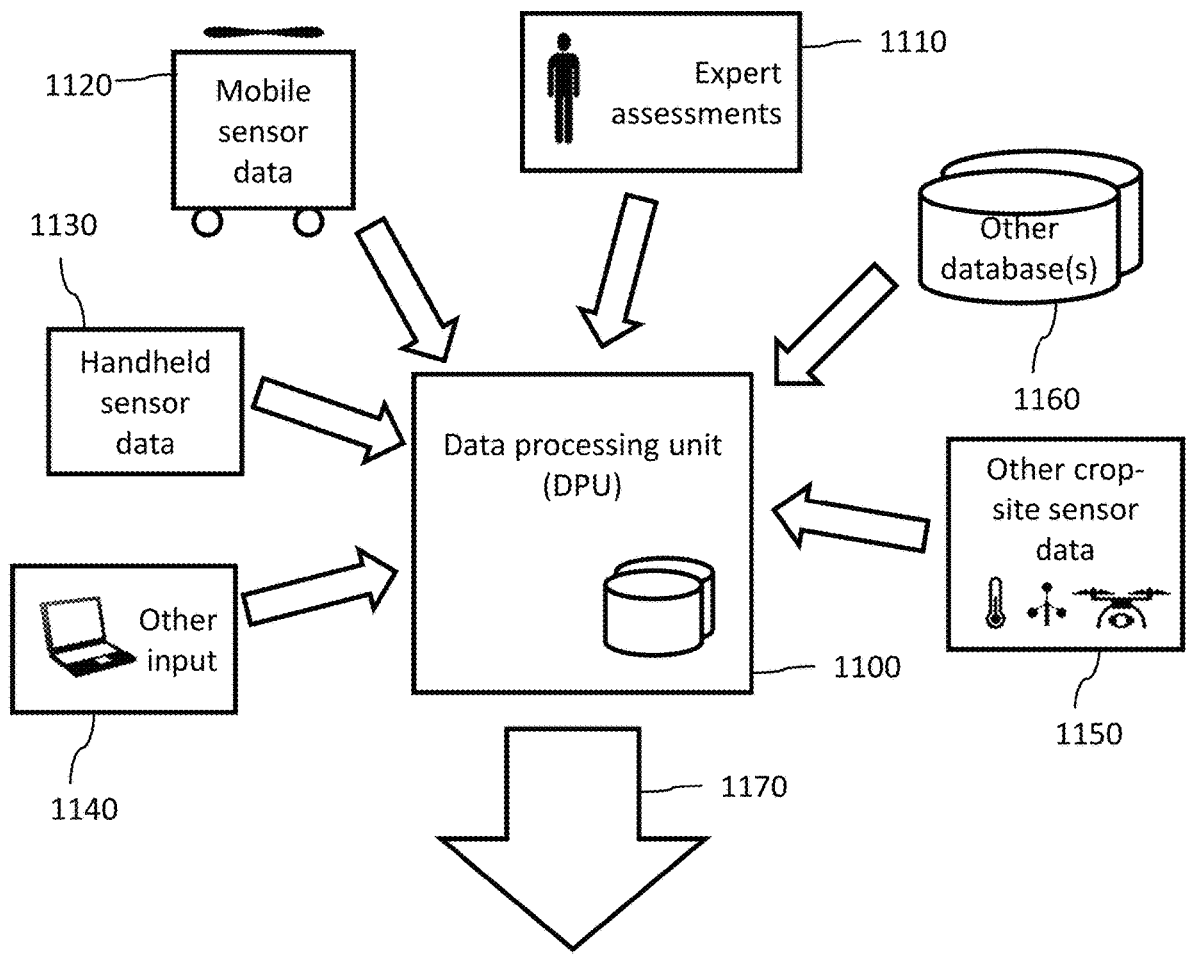
FIG. 11 is a schematic illustration showing various sources of information that may provide inputs to a DPU in embodiments of systems and methods for monitoring and assessing crop health.

As illustrated in FIG. 11, information from other sources can also be employed in embodiments of the systems and methods for monitoring and assessing crop health that are described herein. FIG. 11 shows a DPU 1100 receiving inputs including expert assessments 1110, mobile sensor data 1120, and handheld sensor data 1130 as described above.

DPU 1100 can also receive human input 1140 or input derived from other sources via other devices—for example, personal observations, information about other events that may have affected the crop such as planting, watering and harvesting schedule information. DPU can also receive other crop-site sensor data 1150, for example, from fixed sensors located around the crop-site such as temperature, moisture, light, and air-flow sensors and cameras, and/or from secondary mobile sensors such as drone-mounted sensors. DPU 1100 may also draw on information stored in other databases 1160, such as pre-established scientific models and known indices and standards, or trained data from other crop-sites. This additional input can also be correlated with the expert assessment as described above to generate enhanced trained data.

As described above, DPU 1100 analyzes incoming data and information and provides crop-related information as output 1170.

Learning from Correlation of Future Crop Performance with Past Data

As described above, sensor data can be collected and analyzed, for example, in real-time to classify the current health of a plant. It can also be useful to store and re-analyze such data at a future time. For example, once sensor data is collected for the same plant over a period of time, historical spatiotemporal data can be reverse-engineered or re-analyzed in the context of data that is collected later. Once it is known that a plant is suffering from a problem, it may be possible to retroactively derive patterns or trends from the earlier data for that plant that provided indications that the plant was beginning to deviate from a healthy profile. These clues may exist in the data, even before a less sophisticated data-derived model or an expert would be able to discern a problem. This type of analysis of historical data can be used in the development of predictive models which can then be used to predict health issues and allow intervention before the plant exhibits visible symptoms.

Similarly, over the lifecycle of a crop, a large amount of sensor data and other information is typically gathered and can be stored and reverse-engineered or re-analyzed to provide useful information. The historical data can include:
 expert grower assessments;
 plant-related sensor data, e.g. from handheld devices and mobile sensory platforms;
 data from other sensors monitoring conditions at various locations around the crop-site (for example environmental data such as temperature, light, humidity, wind);
 information about how the crop was managed (for example information about seed source, planting time, irrigation, nutrition, pruning, spraying, harvesting);
 information about specific interventions that were performed in response to crop monitoring.

Information relating to the actual performance of the crop can also be gathered (for example yield, quality, appearance, taste, shelf-life etc.). For example, this can be based on information provided by the grower or other humans (e.g. feedback from customer) and/or data that is captured automatically. Using predictive analytics, this performance information and data can be correlated with data gathered during the lifecycle of the crop to look for patterns and indicators earlier in the crop's lifecycle that are indicative of future performance. For example, by looking at portions of the crop (e.g. specific plants or groups of plants) that performed particularly well or particularly poorly, and analyzing past data for these portions of the crop it may be possible to correlate performance with particular growing conditions (e.g. based on the crop management information and environmental data) and or plant-based sensor data. This information can then be used in the future to try to re-create desirable growing conditions and achieve these over a larger portion of the crop, thereby enhancing performance of the crop in subsequent plantings. Similarly it can be used to identify and try to avoid adverse growing conditions, or to alert the grower when a region of the crop is exhibiting characteristics (e.g. based on monitored sensor data) indicative of future poor performance, so that remedial action can be taken. It can also be used to evaluate the effect of interventions that were performed in trying to mitigate problems with the crop, so that the effectiveness of the interventions can be improved.

Figure 12:
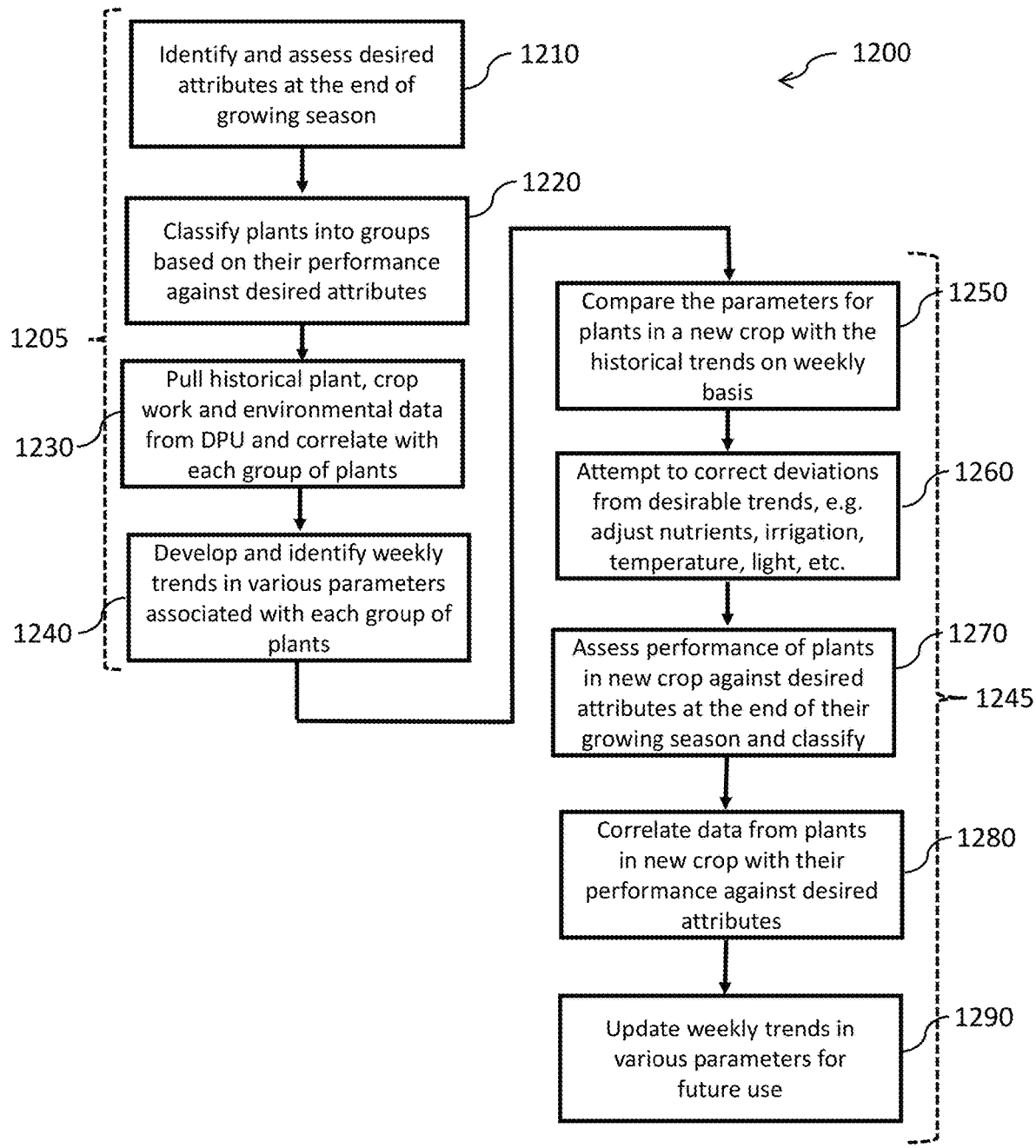
FIG. 12 illustrates an embodiment of a method involving correlation of crop performance data with historical data captured during the lifecycle of the crop.

FIG. 12 is a flow chart illustrating an embodiment of such a process 1200. In a first phase 1205 of process 1200, information relating to the actual performance of a crop is correlated with data gathered during the lifecycle of the crop to identify patterns and indicators. In a second phase 1245, these patterns are then used to attempt to improve the performance of a future crop. At 1210, at the end of a growing season for a particular crop, desired attributes are identified and are assessed for plants in the crop. For example, information relating to yield, taste and other attributes can be collected. At 1220 the plants are classified into groups based on their performance against one or more of these attributes (e.g. high, medium and low performance). At 1230, performance information for the classified groups of plants is correlated with historical data gathered during the lifecycle of the plants to identify patterns. These patterns can be developed into weekly trends for various parameters, at 1240. The trends are associated with the performance level of each group of plants. In the second phase 1245, a new crop is planted and information is captured for plants in the new crop. At 1250, on a weekly basis parameters for plants in the new crop are compared with the historical weekly trends for those parameters that were obtained for the previous crop at 1240. When parameters for particular plants in the new crop begin to show deviation from trends that were previously associated with high performance (desirable attributes), attempts can be made to correct those deviations through various interventions, as shown at 1260. Activities 1250 and 1260 can continue through the growing season for the new crop. At the end of the growing season, the performance of plants in the new crop is assessed with respect to one or more of the desired attributes, and again the plants are classified into groups, as shown at 1270. At 1280, this new performance information is correlated with data gathered during the lifecycle of the plants. At 1290 this information is used to update and improve the patterns and weekly trends that can be used to try to improve the performance of the next crop.

In some implementations of the present technology over 50,000 multi-dimensional data points are collected non-invasively from an individual plant in just a few seconds, allowing physiological, chemical, biological and/or physical changes inside, on the surface and/or around each plant to be detected. Thus, the technology described herein has the potential to capture massive volumes of spatiotemporal data relating to one or more crops over one or more growing seasons. Over time, through machine learning, data mining and/or pattern recognition processes, the DPU can develop specific performance patterns and data-derived models that can be used for classification and analysis of new data. Predictive models can also be developed, that can be used to predict future health or performance of plants in a crop based on their current sensor data. Using predictive models, plants that are on a path towards deteriorating health can be identified based on early clues that can be derived from their current multi-sensor data, in some cases before any single sensor or an expert could detect symptoms of problem. With this early-stage detection, preventative measures can then be taken to try to avoid deterioration in the health and/or improve the performance of the plant.

Deep learning techniques can be used, for example, for feature selection. Feature selection methods can identify attributes in the data that will enhance accuracy of a predictive model, and identify and remove irrelevant and redundant attributes in the data that do not contribute to the accuracy of a predictive model or that may even decrease the accuracy of the model. The large volumes of diverse data that can be generated through crop monitoring, and the potential value of being able to use predictive models for prophylactic intervention to maintain healthy crops, make this application particularly suitable for the application of deep learning techniques.

Generally, the greater the volume of data that is processed, the more robust and accurate the resulting data-derived models and patterns will be. In some aspects, the system can pool the assessments from multiple experts from different farms or sites with respect to a particular type of crop, for example, and then use this combined digitized expertise to enhance the quality and consistency of the data-derived models.

Growers, who are generating and providing crop-related data for development of data-derived models, as well as for automated assessment of their own crops, can then become data entrepreneurs. This is a potential source of revenue generation for growers who opt to sell their generic and non-proprietary crop-related information (such as trends and statistics), for example, to other growers or to the provider of a platform that provides data processing of crop-related data for multiple growers. In one business model, for example, growers may contribute data or statistics to a centralized or shared data-derived model, and then receive a revenue stream based on the amount of their contribution and/or based on the extent to which the model is used for analysis of third party crop-related data.

In some embodiments of the systems and methods described herein, at least some processing and/or analysis of certain types of sensor data is performed on the mobile sensory platform or sensor device itself instead of at a remote DPU. Statistics or information derived from the sensor data, rather than the sensor data itself, is then transmitted to the DPU. This can reduce the volume of data that needs to be transmitted and can increase the overall speed and efficiency of the process. For example, data that is gathered by optical sensors or stereo cameras for the purposes of disparity and depth analysis or verification purposes, could be processed on the mobile sensory platform, and then the relevant information could be transmitted to the DPU along with data from other sensors.

Natural Language Processing

Natural Language Processing (NLP) can be employed in embodiments of the systems and methods described herein, for example, NLP can be incorporated into expert knowledge capture and system training activities and/or information dissemination activities. During expert knowledge capture, verbal assessment of the plants by the expert may be captured and correlated with other input from the expert and sensor data. Different experts might use different words to describe the same situation. For example, the common name of a pest might vary in different locations, yet the terms used may all refer to the same problem. A library of terms and synonyms may be developed and then used. The language and terminology used in disseminating information about plant health maybe automatically adapted based on the geo-location and/or profile of the recipient. The NLP capability can allow experts to describe the condition of a crop verbally while capturing a sensory profile. The same terminology can be used for the reporting app. The NLP may receive and deliver information in various languages.

Mobile Sensory Platform

The mobile sensory platform employed in the systems and methods described above generally comprises more than one type of sensor mounted on a mobile platform. For example, the mobile platform can be a vehicle or cart, such as an automated robot that can patrol between rows of crops, or a drone that can fly over or in between rows of crops. Generally the mobile sensory platform will include a mounting structure such as a scaffold or rack that supports a plurality of sensors and optionally additional probes and/or devices. For example the mobile sensory platform can comprise a mast with attachable, extendable arms, or a column that houses fixed sensors and probes, or a dome that mounts on or under a mobile platform.

Most plants are highly responsive to changes in their surroundings and can convey precise information about their overall health status through those responses. At least some of the sensors that are employed in the mobile sensory platform rely on plant-generated signals or the plants' responses to stimuli to provide indicators of crop health issues. Sensors can be used to obtain information from the plants, and then trained data and associated models generated as described above, can be used to assess and/or predict plant health based on new sensor data.

The mobile sensory platform can comprise some or all of the following types of sensors:

Physiological sensors: these include sensors and probes that can measure physiological performance of crops and/or detect minute changes inside the plant caused by biotic and/or abiotic stressors. For example, chlorophyll fluorescence emitted from the leaves can provide insight into the health of the photosynthetic systems within the plant. Sensors can be used to sense the level of chlorophyll in leaves, and/or photosynthetic efficiency, and/or changes in internal chemical composition related to stress. These sensors can include pulse-modulated optical probes and detectors that stimulate the plant to give a physiological response and then detect that response. The probes might consist of LEDs with specific spectral bands that are used to excite plants and generate various physiological responses that can be correlated to photosynthetic activity or defensive chemicals inside plant foliage. The detectors may be tuned to be responsive to a narrow spectral band that corresponds with specific light that is reflected from or emitted by plants. Generally these sensors will provide the earliest clues that the plant is developing a problem, whereas some of the other sensor types described below will detect changes that occur as a disease, pest or other problem becomes further developed. The reaction of plants to stress typically begins with internal changes in the physiology and chemistry of the plant. This family of sensors can detect those early stage changes and prime the system to conduct further analysis to verify and identify the source of stress.

Surface analysis sensors: these include sensors and probes that can detect changes on the surface of the leaves and other parts of plants, for example, changes in color related to water stress, changes in surface chemistry related to biotic and abiotic stress, physical attributes of leaf surface. Such sensors generally involve spectral detection to detect certain wavelengths of visible (RGB) and near infra-red (NIR) light reflected by the plant. The probes used with these sensors may consist of full spectrum light sources, such as halogen lamps, or probes with narrow spectral bands such as ultraviolet (UV) or near infra-red (NIR). These sensors generally detect secondary stages of changes in plants, caused by stress, that occur on the surface of the foliage.

Chemical sensors: these include sensors and probes that can detect changes in plant-emitted volatile chemicals (e.g. volatile organic compounds, known as VOCs), for example, detecting herbivore-induced volatile compounds emitted by plants while under pest attack. These include photo-ionization detectors (PIDs), surface acoustic wave (SAW) sensors, quartz crystal microbalance (QMB) sensors or other types of chemical sensors that can detect certain compounds down to sub parts per billion concentrations. The chemical volatiles emitted by plants generally convey information about specific biotic stressors.

Thermal sensors: these may include thermal imaging sensors that can give information about surface damage to the foliage or fruit. For example, tiny holes that could be caused by a pest will tend to increase moisture loss and evaporation, resulting in localized lower surface temperatures that can be detected by thermal imaging.

Microclimate sensors: these include sensors and probes that can monitor changes in the microclimate around individual plants, for example, temperature and relative humidity.

Canopy scanning sensors: these include sensors and probes that can detect changes in canopy structure, for example, changes in leaf angle in response to water stress or viral infection. These can include ultrasound and/or LiDaR (light detecting and ranging) type sensors, or stereo-imaging (visible RGB and IR) sensors, for example. Such sensors may be used, for example, to generate disparity maps (providing depth measurement and information about the 3D structure of the plant canopy) which can give information about plant growth. Also they may be used to provide various vegetation indices.

The crop monitoring systems and methods described herein can function with little or no reliance on visual sensors or imaging. In some embodiments, the mobile sensory platform does not comprise cameras or other imaging devices. In other embodiments, one or more cameras or imaging devices are used primarily for verification purposes (e.g. so that a grower can inspect a photographic or video image of a plant that has been assessed by the automated system as having a problem, without having to physically go to the plant to visually inspect it). The imaging devices might be installed on a drone or other flying platforms.

In some embodiments of a mobile sensory platform, the position of some or all of the sensors is adjustable so that they can be positioned appropriately depending on the size (e.g. height and volume) of the plant and which region of the plant is to be sensed. Preferably the sensors can be moved and re-positioned automatically (rather than manually) based on commands from a control system that is responsive to inputs indicative of where the sensors should be positioned.

In some embodiments the mobile sensory platform can further comprise one or more intervention modules for administering remediation to selected plants. Such modules may be mounted to the mounting scaffold to disperse biocontrol agents or other pest and disease management products where and when they are needed.

In some applications, the mobile sensory platform will be charged daily via a stationary charging station installed inside a greenhouse or at the farm. In some cases the charging station can be powered by AC electricity or via solar panels.

The mobile sensory platform can move among the rows of crops. In some embodiments, the mobile sensory platform moves on rails, such as rails that are sometimes installed in greenhouses for other purposes. The platform may detect a rail adjacent to a first row of the plants using one or more sensors and then position itself to move along the rail adjacent to the first row, or may be placed by a staff member at the beginning of a first row within a desired zone. The mobile sensory platform may then move down and back between each pair of rows of plants (assuming they are dead-ended rows) until it covers all the rows in the zone. Specific rail detecting sensors or positioning beacons can be used to guide the mobile sensory platform from one row to another. At the end of the mission, the platform may move itself to the charging station following a pre-programmed route or may remain at the end of its path to be moved by a staff member in the morning.

Figure 13A:
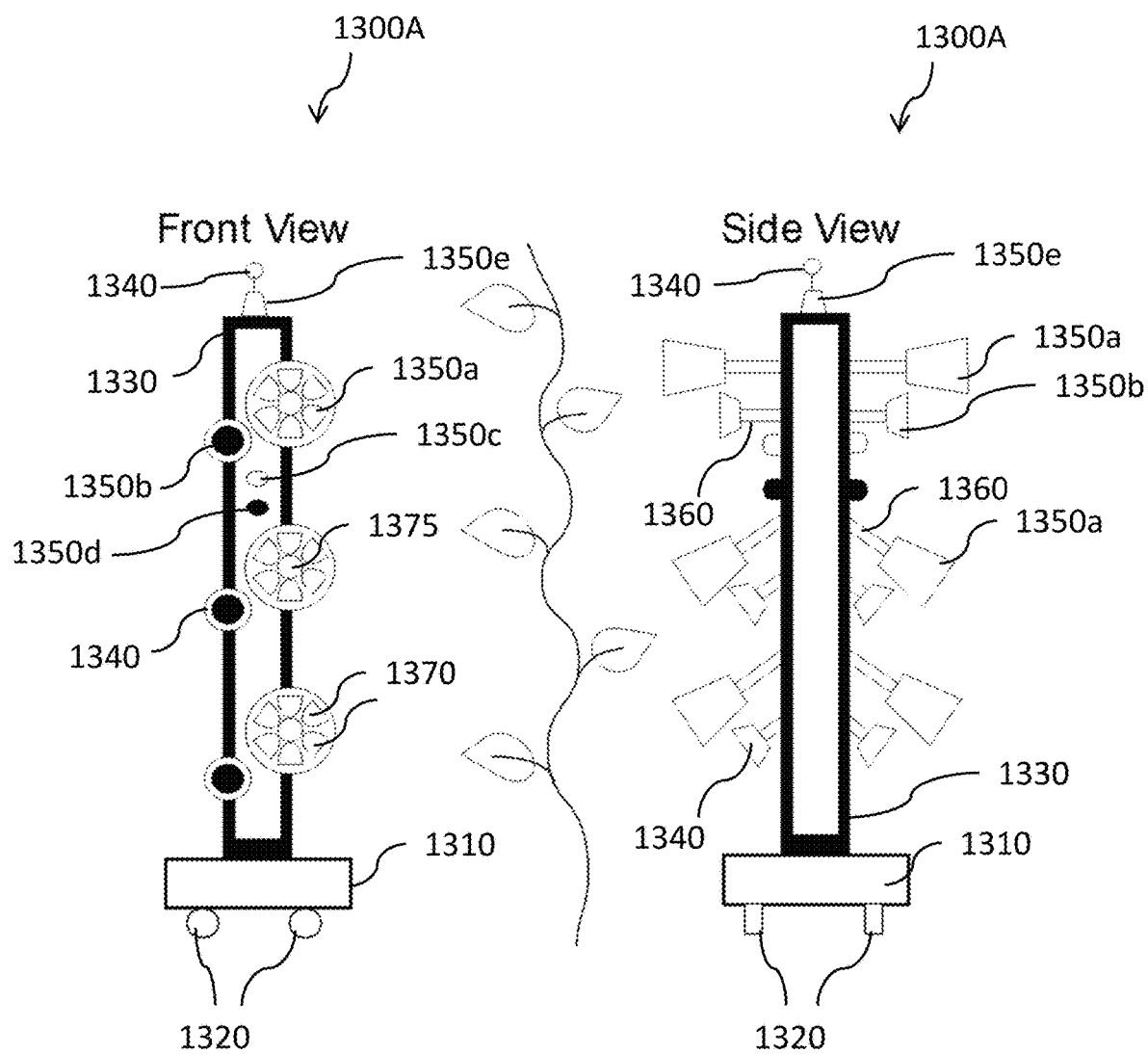
FIG. 13A is a simplified drawing showing a front view and a side view of an embodiment of a mobile sensory platform.
Figure 13B:
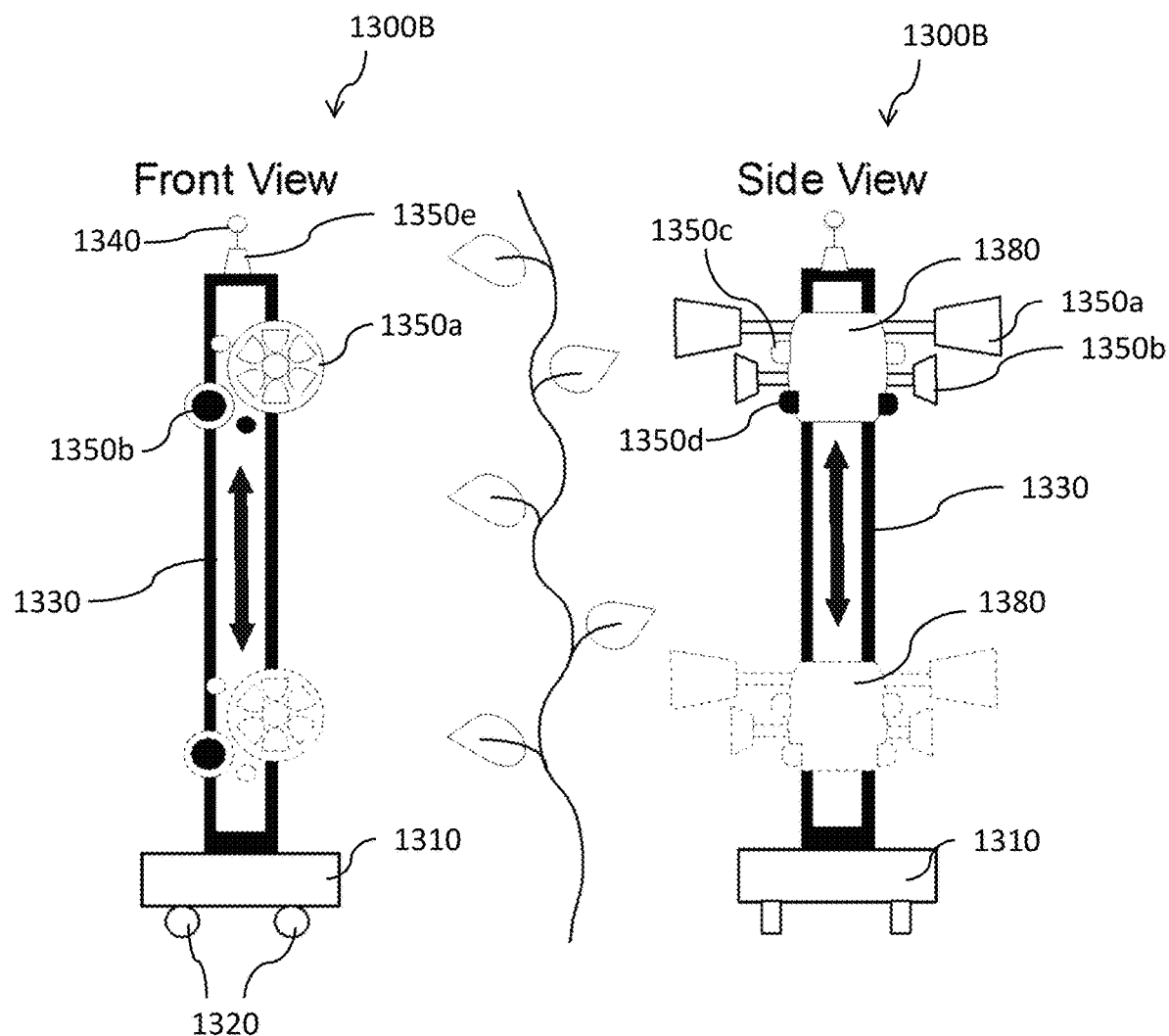
FIG. 13B is a simplified drawing showing a front view and a side view of another embodiment of a mobile sensory platform.
Figure 13C:
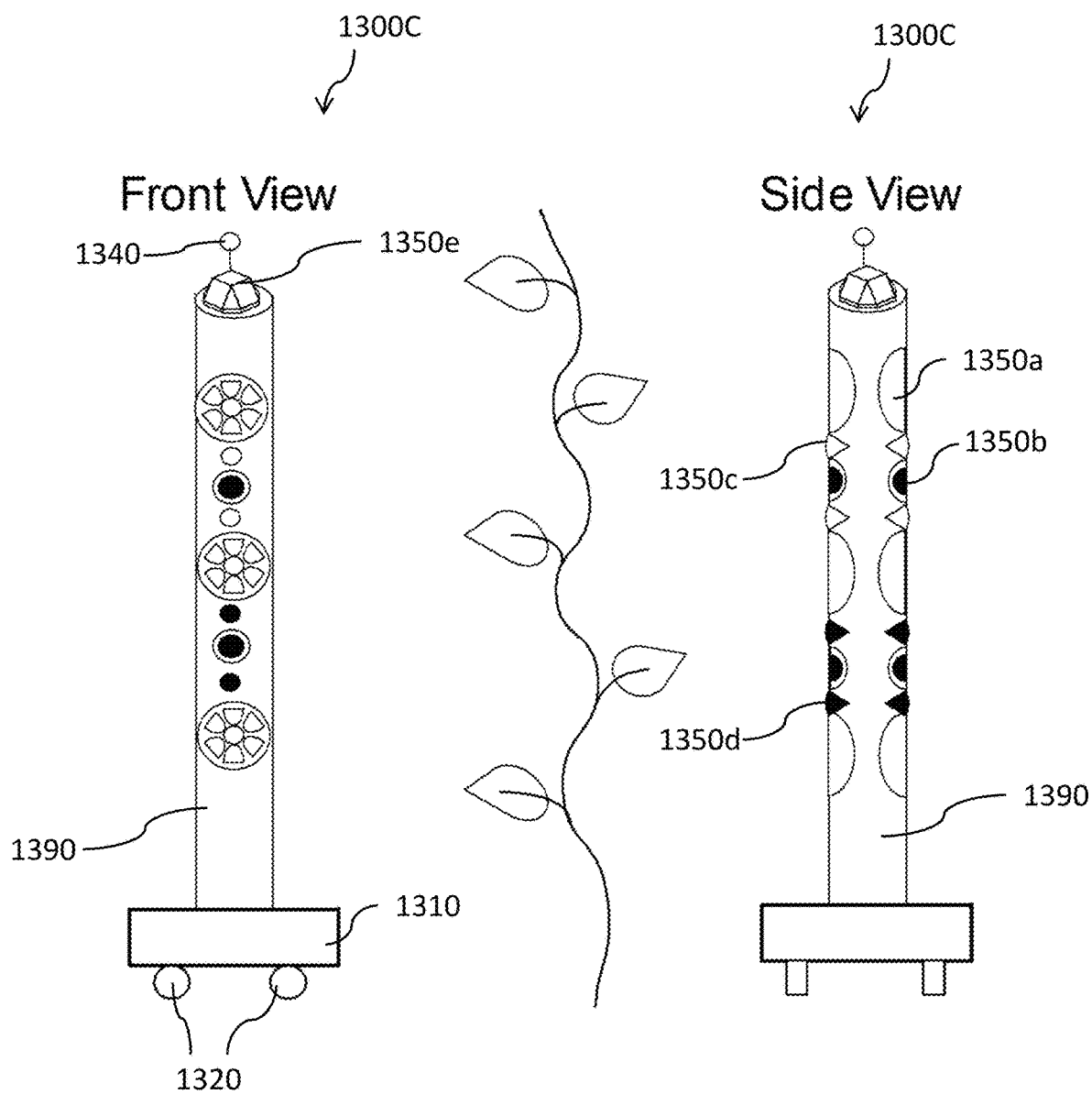
FIG. 13C is a simplified drawing showing a front view and a side view of yet another embodiment of a mobile sensory platform.

Some example embodiments of mobile sensory platforms that can be employed in the systems and methods described herein are illustrated in FIGS. 13A, 13B and 13C, each of which shows a front view and a side view of a mobile sensory platform.

FIG. 13A is a simplified drawing showing two orthogonal views of a mobile sensory platform 1300A having a base 1310 and wheels or rollers 1320 that can move around on the ground and/or on rails. Mobile sensory platform 1300A includes a mounting scaffold 1330 to which a plurality of sensors 1350a-e can be attached. Mounting scaffold 1330 is equipped with a data transmission mechanism 1340 that can be placed in various locations on mounting scaffold 1330. In the illustrated embodiment a variety of sensor types are attached at various locations on mounting scaffold 1330: physiological sensors 1350a, chemical sensors 1350b, microclimate sensors 1350c, surface analysis sensors 1350d and a canopy scanning sensor 1350e. Physiological sensors 1350a and chemical sensors 1350b can be placed on a rotating arm 1360 that moves both vertically and horizontally on an anchor. Physiological sensors 1350a include excitation probes 1370 and a signal detector 1375. Mobile sensory platform can be automated and self-powered so that it moves around the greenhouse or field under the control of a control system.

FIG. 13B and FIG. 13C illustrate mobile sensory platforms 1300B and 1300C, respectively, that are similar to mobile sensory platform 1300A that is illustrated in FIG. 13A, but with different mounting structures. In FIG. 13B and FIG. 13C the same numbers are used to label elements that are the same as or similar to those referred to in the description of FIG. 13A.

In mobile sensory platform 1300B of FIG. 13B a sliding actuator 1380 is attached to mounting scaffold 1330 and moves up and down vertically (shown with dashed lines in a lower position). The positioning of actuator 1380 can be based on input from one or more of the sensors (e.g. indicative of the height of the plant or the location of the region of interest on or around the plant). The sliding actuator 1380 carries physiological sensors 1350a, chemical sensors 1350b, microclimate sensors 1350c and surface analysis sensors 1350d.

Mobile sensory platform 1300C of FIG. 13C comprises a cylindrical mounting scaffold 1390 that houses the physiological sensors 1350a, chemical sensors 1350b, microclimate sensors 1350c, surface analysis sensors 1350d, and canopy scanning sensor 1350e. Cylindrical mounting scaffold 1390 is attached to the ground mobility platform 1310. Cylindrical mounting scaffold 1390 protects the sensors that are placed in various locations inside it.

Figure 14A:
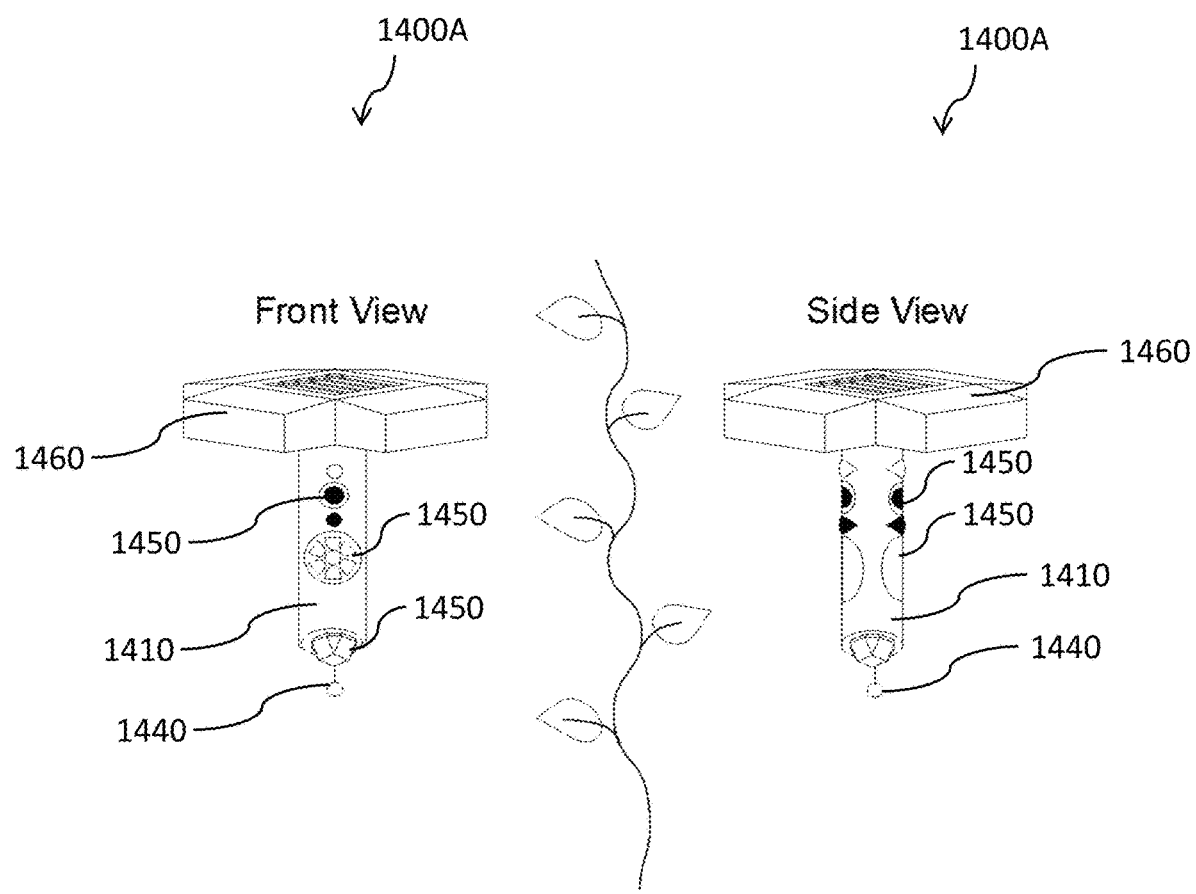
FIG. 14A is a simplified drawing showing two views of an embodiment of an air-borne mobile sensory platform.

FIG. 14A is a simplified drawing showing two views of an air-borne mobile sensory platform 1400A that carries a suspended sensory scaffold 1410. Various sensors 1450 are attached to suspended sensory scaffold, similar to sensors 1350a-d. Sensory platform 1400A also includes data transmission mechanism 1440. Housing 1460 accommodates a propulsion mechanism (not visible) which can include one or more propellers and a motor.

Figure 14B:
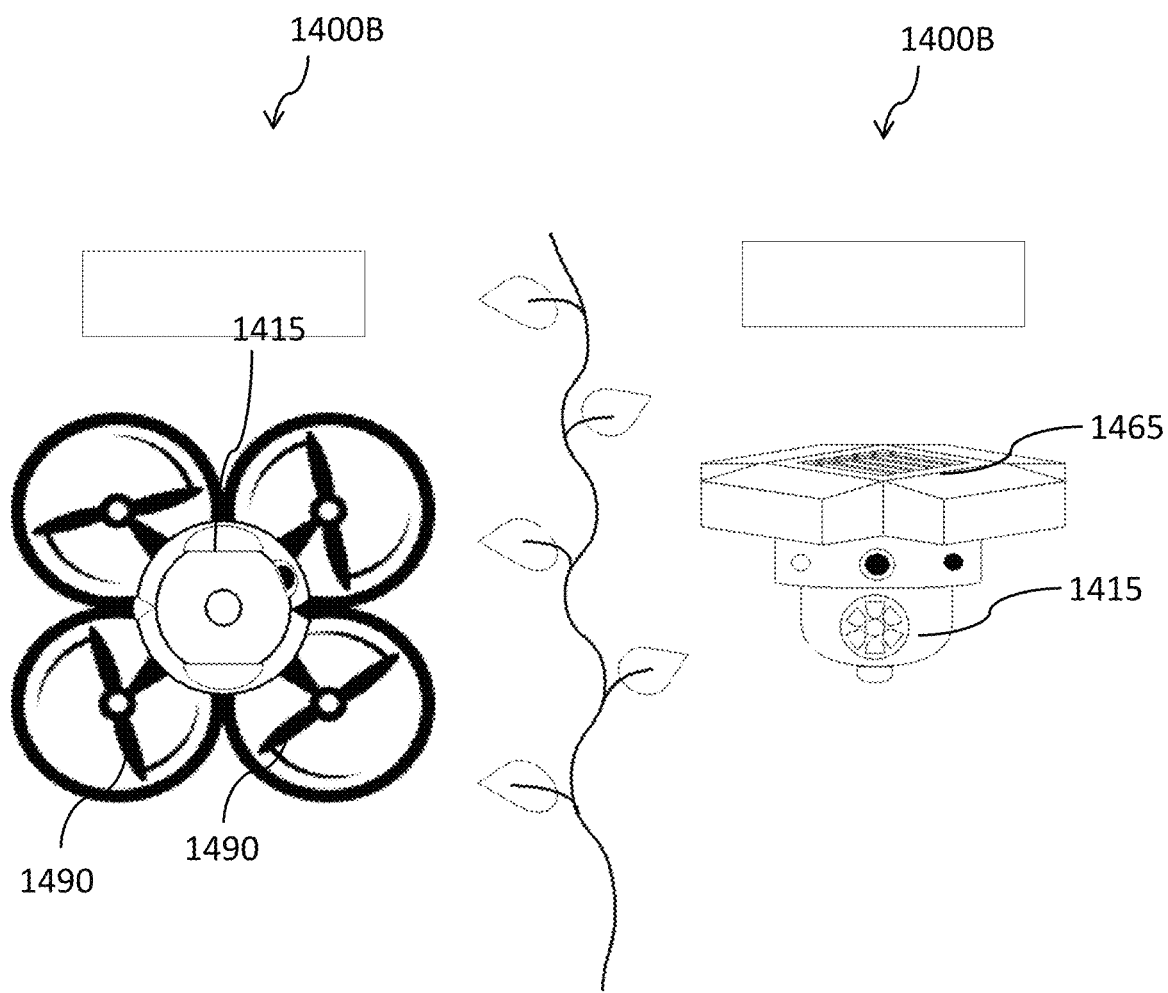
FIG. 14B is a simplified drawing showing two views of an embodiment of an air-borne mobile sensory platform.

FIG. 14B is a simplified drawing showing two views of another air-borne mobile sensory platform 1400B comprising a dome 1415 positioned underneath housing 1465. Dome 1415 houses various sensors similar to those described above, and housing 1465 accommodates a propulsion system including four propellers 1490.

Figure 14C:
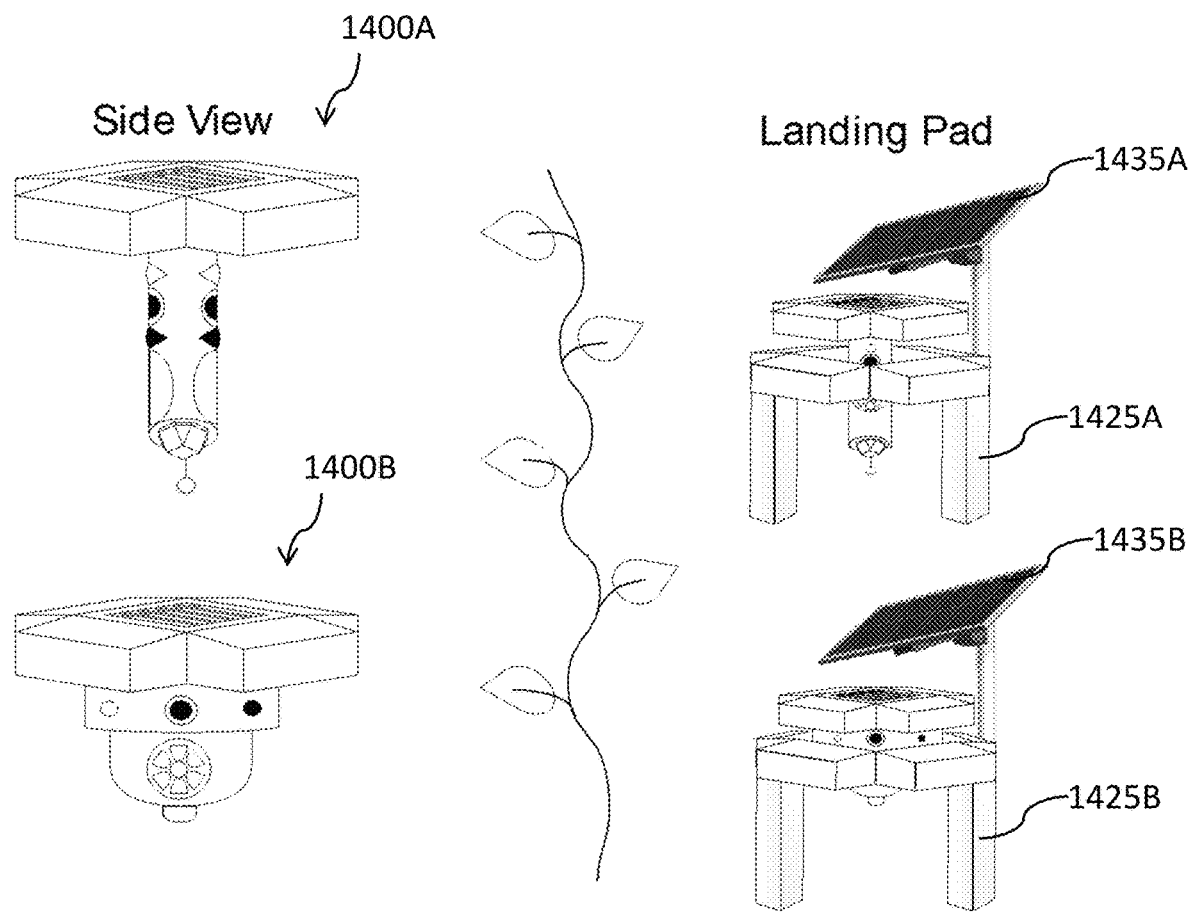
FIG. 14C is a simplified drawing showing embodiments of a landing pad where the air-borne mobile sensory platforms of FIGS. 14A and 14B can land for recharging.

In some embodiments the mobile sensory platform further comprises a docking station or similar device where the device can be re-charged. For example, FIG. 14C shows a landing pad 1425A and 1425B where an airborne mobile sensory platform, such as 1400A of FIG. 14A or 1400B of FIG. 14B, respectively, can land and charge its batteries. The landing pads are 1425A and 1425B are each fitted with a solar panel 1435A and 1435B respectively, that harvests solar energy and turns it in to electrical power that is used to charge the airborne mobile sensory platform. In some embodiments an air-borne mobile sensory platform (such as a drone) can dock with another mobile sensory platform (such as a cart or rover robot) for recharging and/or data transfer purposes. For example, the landing pad could be on another mobile sensory platform.

Hand-Held Device for Expert Knowledge Capture

Figure 15A:
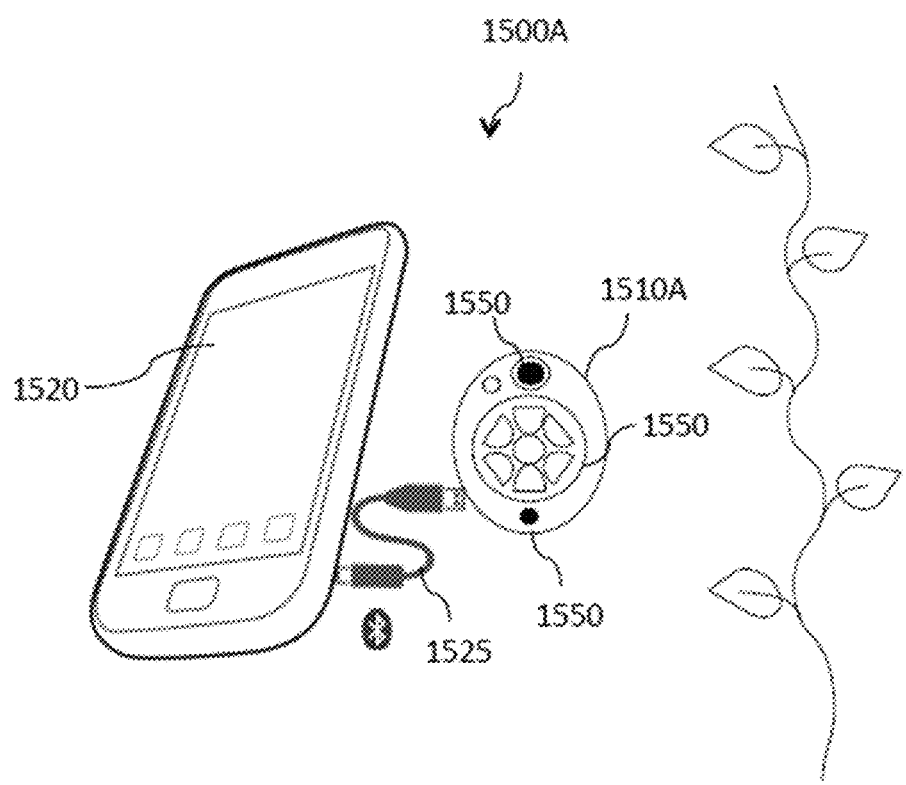
FIG. 15A is a simplified drawing of an embodiment of a hand-held device comprising a portable sensory platform connected to a smartphone.
Figure 15B:
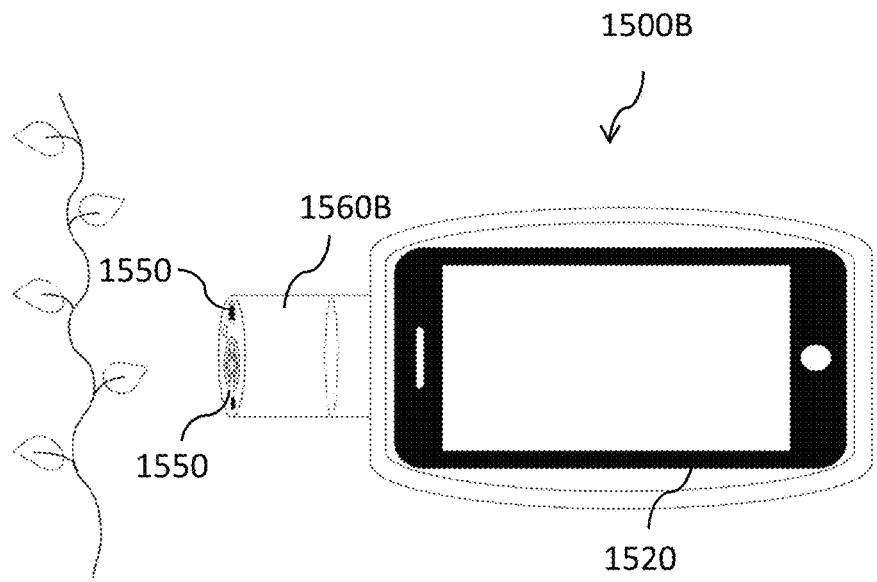
FIG. 15B is a simplified drawing of another embodiment of a hand-held device comprising a portable sensory platform connected to a smartphone.
Figure 15C:
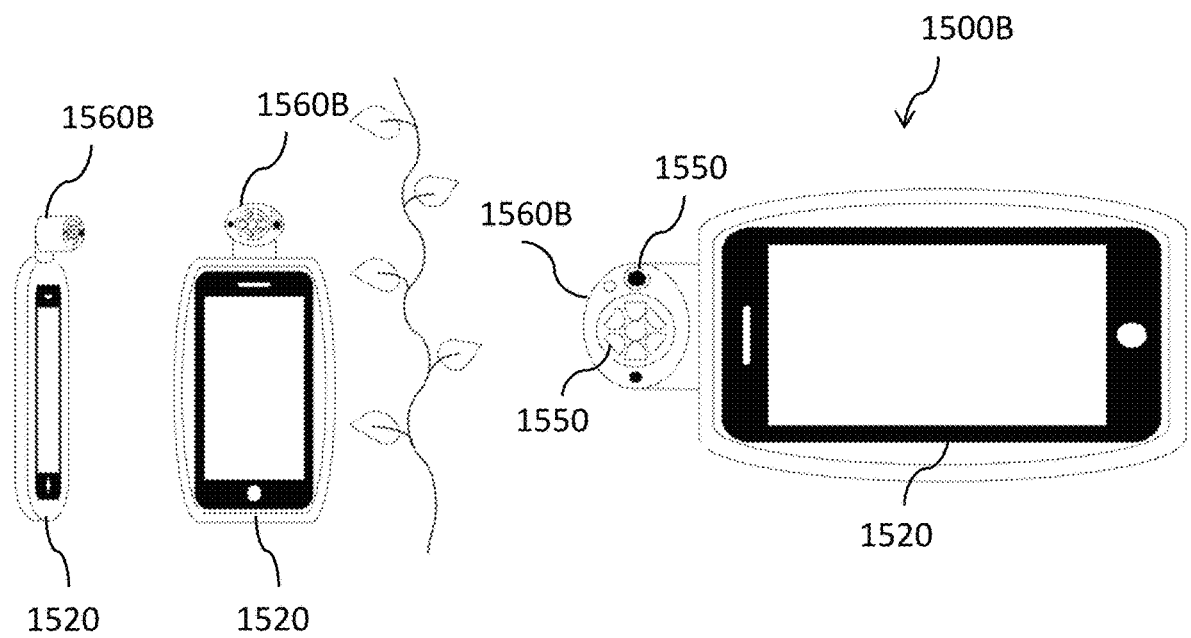
FIG. 15C is a simplified drawing showing three views of yet another embodiment of a hand-held device comprising a portable sensory platform connected to a smartphone.

In addition to a mobile sensory platform, hand-held devices can be employed in the systems and methods described herein in order to capture human knowledge. Some example embodiments of hand-held devices that can be employed in systems and methods as described herein are illustrated in FIGS. 15A, 15B and 15C. In some systems a hand-held multi-sensor device is also mountable to a mobile platform so that it can be used by a person or as part of an automated crop monitoring system (see FIGS. 16 and 17 below, for example).

FIG. 15A shows a simplified drawing of an embodiment of a hand-held device 1500A comprising a portable sensory platform 1510A that houses various sensors 1550. Portable sensory platform 1510A connects to a smartphone or tablet 1520 either wirelessly or by wire 1525.

FIGS. 15B and 15C are simplified drawings of various views and configurations of another embodiment of a hand-held device 1500B comprising a multi-sensor module 1560B that houses various sensors 1550 connects to a smartphone or tablet 1520.

Multi-sensor module 1560B is equipped with a set of sensors that can be positioned in two configurations. In the first configuration, shown in FIG. 15B sensors 1550 are oriented in-line with the smartphone 1520 (i.e. directed in the plane of the phone). This allows the user to point the sensors on device 1500B toward a plant and enter their assessment of the health of the plant using smart phone 1520, based on their expert knowledge. For example, in an assessment mode, an app on the phone may instruct an expert user to point the sensors toward the plant, click a run button to record sensor data, and immediately or simultaneously enter their expert assessment in response to multiple options related to the health of the plant. In one non-limiting example of the functionality of app, the multiple choices may be depicted by colored circles, for example, red for unhealthy, orange for moderately healthy and green for healthy. In another non-limiting example of the functionality of app, detailed multiple-choice questions may guide an expert user to assess the health of plant.

A second configuration of handheld device 1500B is shown in FIG. 15C where sensors 1550 on multi-sensor module 1560B are oriented in a perpendicular position relative to the plane of smartphone 1520. Multi-sensor module 1560B includes a pivot mechanism to allow this change in configuration. In this configuration handheld device 1500B can be inserted into or clipped to a shirt pocket, for example. A non-expert can carry module 1560B in this way so that sensors 1550 is directed toward the plants and can capture sensor data as the non-expert performs routine tasks. The data may be processed by a DPU and information or alerts sent back to the non-expert in real-time via device 1560B as described above.

Modular Multi-Sensor Device

Figure 16A:
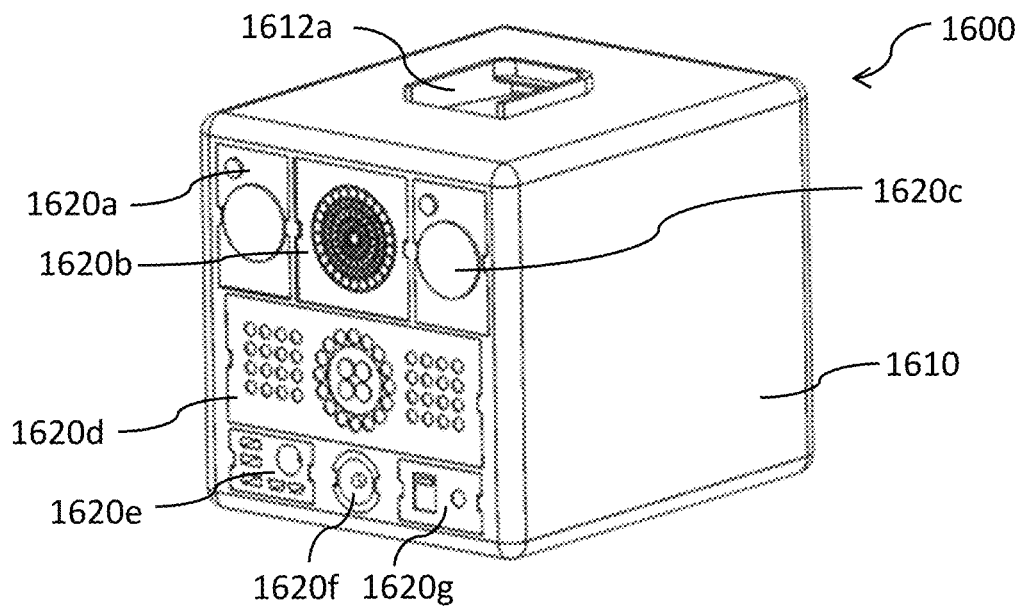
FIG. 16A illustrates an embodiment of a modular multi-sensor device, for crop monitoring, that can be used as a hand-held device or can be mounted to a mobile platform.
Figure 16B:
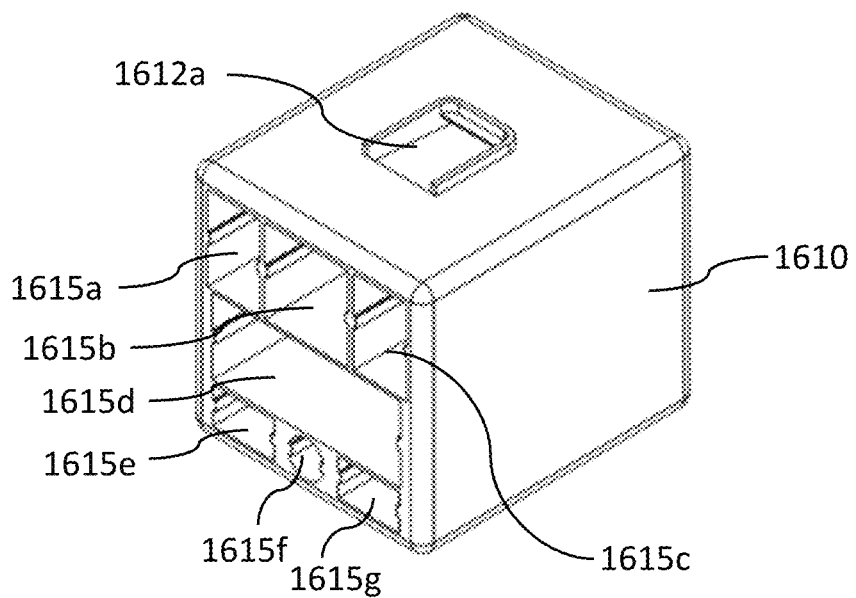
FIG. 16B illustrates a housing that can accommodate various sensor modules and other components
Figure 16C:
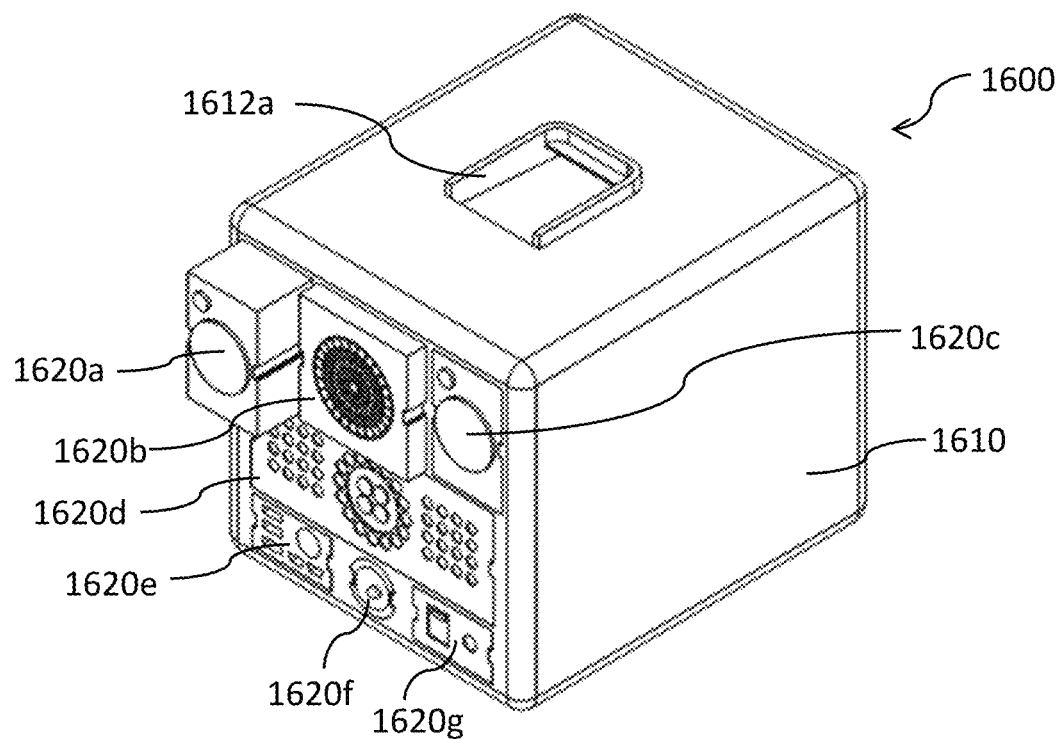
FIG. 16C shows the multi-sensor device of FIG. 16A with some of the sensor modules partially removed by sliding out of housing.
Figure 16D:
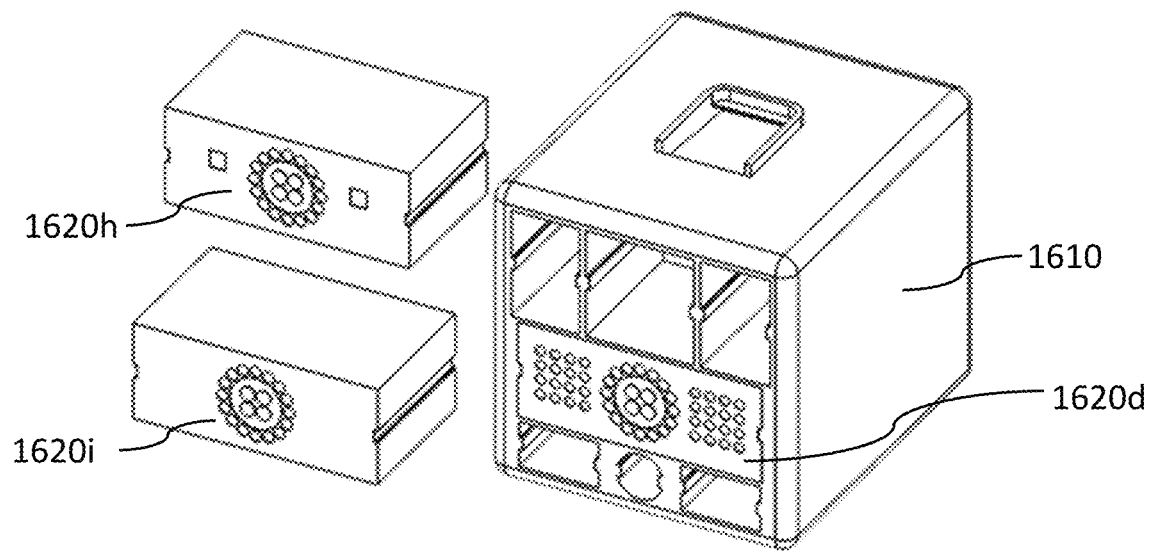
FIG. 16D shows a housing with a sensor module installed in the housing position, and two alternative sensor modules which can replace the installed sensor module.

FIG. 16A shows an embodiment of a multi-sensor device 1600, for crop monitoring, that can be used as a hand-held device or can be mounted to a mobile platform. Multi-sensor device 1600 comprises a housing 1610 and removable sensor modules 1620*a-g* that are slotted into housing 1610. FIG. 16B shows housing 1610 with the sensor modules removed, and shows interior slots or cavities 1615*a-g* that can accommodate various sensor modules. Housing 1610 has a mount 1612*a* on its upper exterior surface and a similar mount 1612*b* (not visible) on its lower exterior surface. FIG. 16C shows multi-sensor device 1600 with sensor modules 1620*a* and 1620*b* partially removed by sliding out of housing 1610. Each sensor module can be replaced with a different module having the same form factor, or optionally with a blank or cover to close off the cavity. Housing 1610 can be constructed from any suitable material or materials including for example, various plastics and/or metals. If the device is to be used outdoors the materials are preferably waterproof, weatherproof and heat-resistant to withstand harsh environmental conditions. FIG. 16D shows housing 1610 with sensor module 1620*d* installed, and two alternative sensor modules 1620*h* and 1620*i* which can replace sensor module 1620*d*. Multi-sensor device 1600 incorporates a variety of sensors in a space-efficient manner into a compact, portable device.

Sensor modules 1620*a-g* can be different types of sensors that can be used to sense and provide sensor data for plant-related parameters in a crop monitoring system. The sensor modules may screw, snap, lock, or be otherwise secured in the housing. Preferably they can be removed and replaced manually or via a simple mechanism. The sensor modules are connected to a universal adapter at the rear of the housing.

Figure 16E:
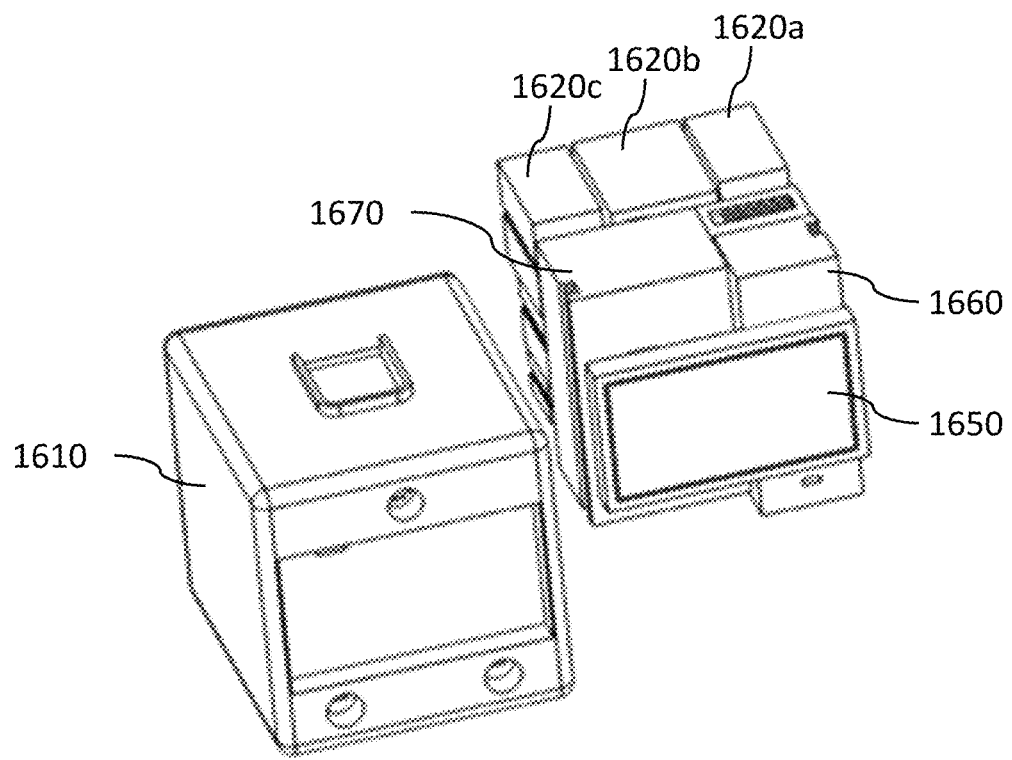
FIG. 16E shows a rear perspective view of the housing shown in FIG. 16B, and shows separately a bundle of components that can be installed in the housing.

FIG. 16E shows a rear perspective view of housing 1610 shown in FIG. 16B, and shows separately the bundle of components that is housed in housing 1610 when the multi-sensor device 1600 is assembled. As well as sensor modules, the components include a communications system/interface module 1660 comprising an LCD touch-screen display 1650 (for use as a user interface), and a master control unit (MCU) 1670 comprising a processor and associated software. Multi-sensor device 1600 comprises a universal adaptor (not shown) to which all of the sensor modules 1620*a-g* can connect. The universal adapter provides power, data and control signal connectivity between the sensor modules and MCU 1670, regardless of the connector or port on the sensor. On MCU 1670 there is a device driver associated with each sensor.

Figure 17A:
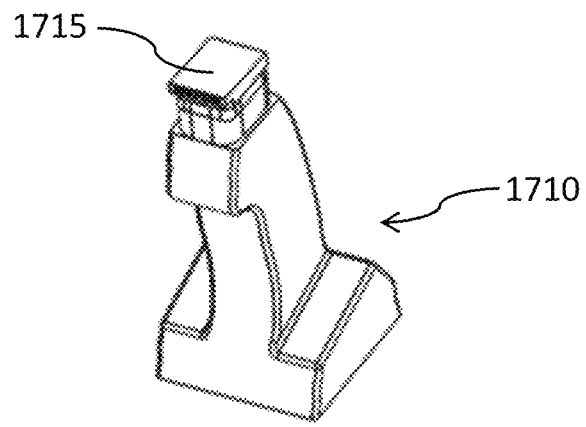
FIG. 17A shows an example of handle that can be fastened to the multi-sensor device of FIG. 16A.
Figure 17B:
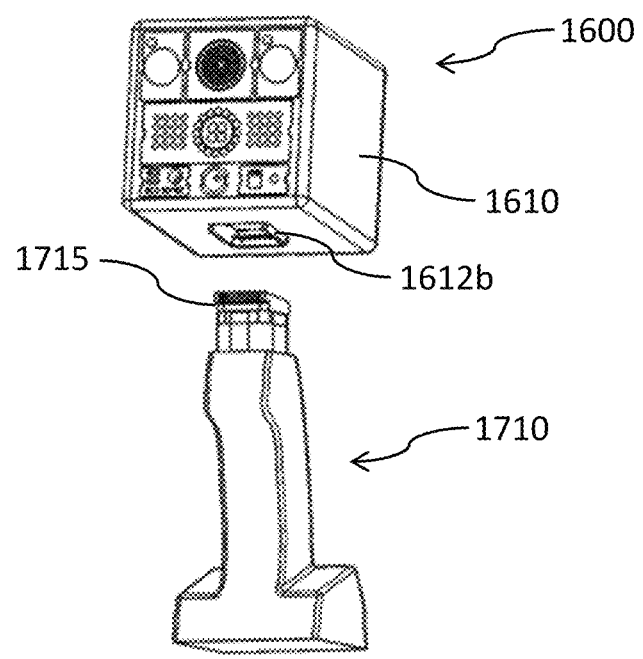
FIG. 17B illustrates how the handle of FIG. 17A can be fastened to the multi-sensor device of FIG. 16A.
Figure 17C:
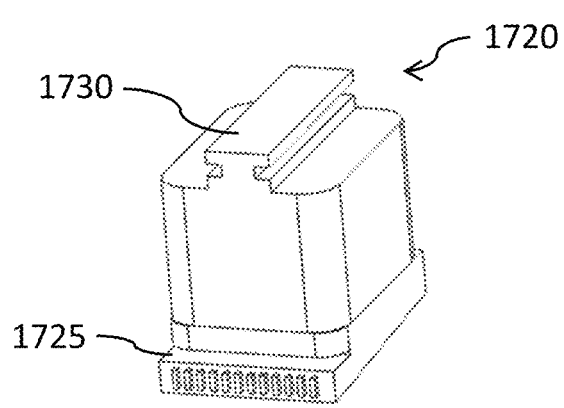
FIG. 17C illustrates a mounting connector that can be removably fastened to a mount on the exterior of a multi-sensor device.
Figure 17D:
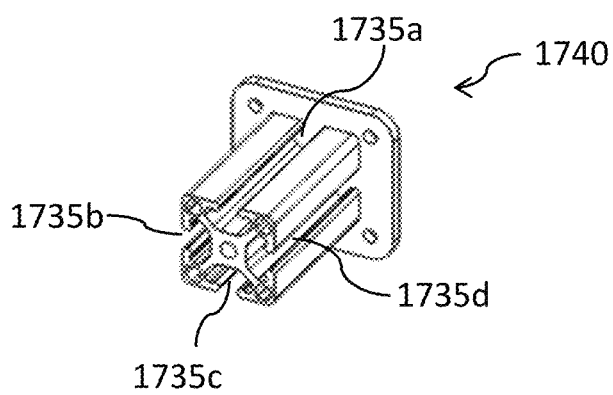
FIG. 17D illustrates a mounting bracket via which a multi-sensor device can be mounted to a mobile platform.
Figure 17E:
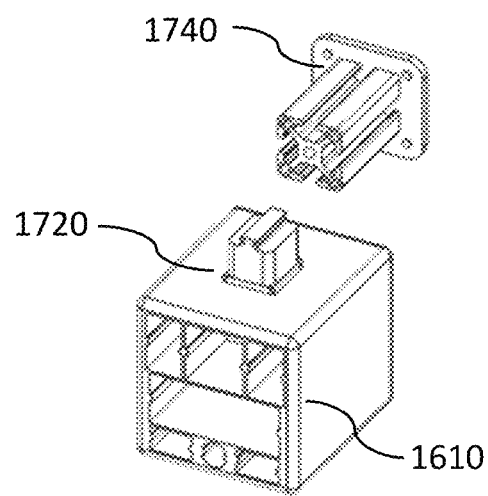
FIG. 17E illustrates how the multi-sensor device housing of FIG. 16B can be mounted to the bracket of FIG. 17D.

Multi-sensor device 1600 can be mounted to a handle for use as a hand-held device, or can be mounted to a mobile platform such as a vehicle, cart, robot, drone, or zip-line harness for automated use. FIG. 17A shows an example of handle 1710 having a mounting connector 1715 which can be snapped into or otherwise removably fastened to mount 1612*b* on housing 1610 of multi-sensor device 1600, as illustrated in FIG. 17B. FIG. 17C shows a mounting connector 1720 that can be snapped into or otherwise removably fastened to mount 1612*a* or 1612*b* on housing 1610 via portion 1725. Mounting connector 1720 includes tongue 1730 that can be slide-mounted into any of four corresponding grooves 1735*a-d* on a mounting bracket 1740 shown in FIGS. 17D and 17E. Bracket 1740 can be connected to or integrated into a mobile platform. Multi-sensor device can be mounted so that is side-facing, upward-facing, downward-facing or at a desired angle relative to the plants. Housing 1610 may have additional mounts on it. Mounting connectors 1715 or 1720, or bracket 1725 may include a pivot mechanism, so that the angle of orientation of the multi-sensor platform relative to the plants can be adjusted.

Mounts 1612*a* and 1612*b* also serve as power connectors via which an external power source can be connected to provide electrical power to the multi-sensor device 1600. For example, handle 1710 can comprise a rechargeable battery or, if the device is mounted to a mobile platform, it can be connected to receive power from a power source on-board the device.

Housing 1610 can be populated with different sensor modules. This modularity and flexibility makes multi-sensor platform versatile easily adaptable for different crop-sensing applications. In one implementation, a multi-sensor device comprises the following modules contained within a single housing:
  (a) a physiological sensor module comprising configurable optical probes and tunable detectors;
  (b) a surface analysis sensor module comprising a full spectrum light source (for example, a halogen lamp) as the probe, and spectroscopic detectors;
  (c) a chemical analysis sensor module comprising a photo-ionization detector (PID), or a surface acoustic wave (SAW) sensor, or a quartz microbalance crystal (QMB) sensor;
  (d) a thermal imaging sensor module which can produce a graphical heat map of the surface of a plant;
  (e) a vision system module comprising a pair of high resolution RGB-IR cameras for stereo-imaging, and infra-red distance sensors the output of which can be used to calibrate the stereo images; and
  (f) an environmental measurement module comprising temperature and humidity sensors to evaluate the microclimate of the area surrounding a plant.

A single plant can be assessed using all of the sensor modules in the multi-sensor device within a few seconds or less.

In the physiological sensor module, the optical probes can comprise LEDs with specific spectral bands that are used to excite plants and generate various physiological responses. An optical detector array can incorporate multiple-wavelength optical detectors selected or tuned to be responsive to a narrow spectral band that corresponds with specific light that is reflected from or emitted by the plants.

FIG. 16D shows three physiological sensor modules 1620d, 1620h and 1620i with different configurations of LEDs and detectors. Module 1620d has four central detectors (these could be blue, yellow, red and far red detectors, for example) surrounded by a ring of LED probes, with another array of LED probes on each side. The specific LEDs and detectors can be selected and changed to suit a specific crop or to obtain information about a specific condition. Again, this provides flexibility and versatility to the device.

The MCU controls the sequence and spacing of the LED pulses, pulse duration, pulse intensity and the number of LED pulses that are used to stimulate the plant in a particular assessment. The optical detectors receive reflected and emitted light from the plant to excitation light and generate a low-level current. The current is significantly amplified (for example, up to $10^7$ times), and filtered before being digitized. In one example, the plant is stimulated with a series of one hundred 100 microsecond pulses of RGB-UV-NIR light separated by 25 millisecond gaps, and at least 4 detectors are used to measure light reflected and emitted from plants.

Analog front-end (AFE) circuitry that allows the user to switch between "day" and "night" modes can be incorporated into the MCU of the multi-sensor device. Once set in day mode, the AFE filters out ambient light, thereby enabling detection of extremely low levels of response light (signal) in the presence of high intensity ambient light (noise). The night mode is adapted or optimized for measurements in low ambient light (noise) intensity. The processed AFE response (amplified and filtered) is digitized by a multi-channel high-speed (e.g. 2 mega samples per second) high-resolution (e.g. 16-bit) analog-to-digital converter (ADC). The optical detector system measures discreet wavelength bands at very high speeds. Optical readings and digitized data are transmitted via the communications system/interface. During further processing of the data, mathematical manipulation can be used to eliminate distance and uneven surfaces as factors in the response data. For example, if the detectors and light probes are in the same plain, a ratio of measurements in correlation to each other can be used to overcome the issue of the distance. For example, instead of comparing a sensor A reading from plant 1 to plant 2, the ratio of a pair of sensor readings (sensor A reading/sensor B reading) for each of the two plants can be compared. This way, although the individual sensor readings might vary from plant to plant based on the distance between the plant and the sensor, comparison of the ratios will provide meaningful comparison between plants.

During operation of the surface analysis sensor module, the full spectrum light source is also activated during a light emission period, and spectroscopic detectors measure the entire wavelength from NIR to UV at high resolution, but at lower speed than for the physiological sensing. Spectroscopy readings are transmitted via the communications system/interface.

During operation of the chemical analysis sensor module, the chemical sensor detects VOCs produced by the plant down to sub ppb levels, and produces a voltage in response to the compound concentration level. The output voltage is digitized by a high-resolution analog-to-digital converter (ADC) and the data is transmitted via the communications system/interface.

Embodiments of the technology, devices, systems and methods described herein can be used separately or can be used in various combinations as desired.

While particular elements, embodiments and applications of the present invention have been shown and described, it will be understood, that the invention is not limited thereto since modifications can be made by those skilled in the art without departing from the scope of the present disclosure, particularly in light of the foregoing teachings.

What is claimed is:

1. A method comprising:
    receiving, using at least one processor, first sensor data pertaining to plant-related parameters of each of one or more first plants that performed well over time;
    analyzing, using the at least one processor, at least some of the first sensor data to generate a predictive model associated with the one or more first plants;
    receiving, using the at least one processor, second sensor data pertaining to plant-related parameters of each of multiple second plants;
    identifying, using the at least one processor, at least one of the second plants to receive one or more interventions by applying the predictive model to the second sensor data, wherein identifying the at least one of the second plants comprises identifying the at least one of the second plants as having at least one of the plant-related parameters that deviates from at least one of the plant-related parameters of the one or more first plants; and
    causing the one or more interventions involving the at least one identified second plant to be performed.

2. The method of claim 1, wherein the one or more interventions are selected to increase a predicted future performance of the at least one identified second plant towards a performance of the one or more first plants.

3. The method of claim 1, wherein the one or more interventions comprise at least one of: dispersion of a bio-control agent, activation of an irrigation system, adjustment of a temperature control system, or administration of a nutrient or a pesticide.

4. The method of claim 1, further comprising:
    outputting, to a user, a notification identifying the one or more interventions involving the at least one identified second plant.

5. The method of claim 1, wherein the second sensor data comprises canopy sensor data from one or more canopy scanning sensors, the canopy sensor data comprising information about a three-dimensional structure of each of the second plants.

6. The method of claim 1, wherein the second sensor data comprises data from one or more cameras that capture images of the multiple plants.

7. The method of claim 1, wherein the second sensor data comprises data from (i) multiple cameras that capture stereo images of the multiple plants and (ii) distance sensors that capture distance measurements for calibrating the stereo images.

8. The method of claim 1, further comprising:
    generating a graphical user interface that includes a graphical representation of a growing area associated with the second plants; and
    identifying, using one or more markers in the graphical representation of the growing area, one or more locations of the at least one of the second plants.

9. The method of claim 8, wherein:
    each of the one or more markers is selectable by a user; and the method further includes, in response to a selection of a specified marker among the one or more markers, presenting in the graphical user interface information associated with the second plant at a location associated with the specified marker.

10. The method of claim 1, wherein the second sensor data is received from one or more microclimate sensors positioned on a mobile platform, the one or more microclimate sensors configured to generate microclimate sensor data based on a microclimate around individual ones of the second plants.

11. The method of claim 1, wherein the predictive model is generated using machine learning.

12. The method of claim 1, wherein analyzing at least some of the first sensor data to generate the predictive model comprises:
performing feature selection to identify attributes in the first sensor data that enhance an accuracy of the predictive model;
excluding any of the first sensor data that does not contribute to the accuracy of the predictive model or that decreases the accuracy of the predictive model; and
generating the predictive model based on the identified attributes and not based on the excluded first sensor data.

13. An apparatus comprising:
at least one interface configured to receive first sensor data pertaining to plant-related parameters of each of one or more first plants that performed well over time; and
at least one processor configured to:
analyze at least some of the first sensor data to generate a predictive model associated with the one or more first plants;
receive second sensor data pertaining to plant-related parameters of each of multiple second plants;
identify at least one of the second plants to receive one or more interventions by applying the predictive model to the second sensor data; and
cause the one or more interventions involving the at least one identified second plant to be performed;
wherein, to identify the at least one of the second plants, the at least one processor is configured to identify the at least one of the second plants as having at least one of the plant-related parameters that deviates from at least one of the plant-related parameters of the one or more first plants.

14. The apparatus of claim 13, wherein the at least one processor is configured to select the one or more interventions in order to increase a predicted future performance of the at least one identified second plant towards a performance of the one or more first plants.

15. The apparatus of claim 13, wherein the one or more interventions comprise at least one of: dispersion of a bio-control agent, activation of an irrigation system, adjustment of a temperature control system, or administration of a nutrient or a pesticide.

16. The apparatus of claim 13, wherein the at least one processor is further configured to output, to a user, a notification identifying the one or more interventions involving the at least one identified second plant.

17. The apparatus of claim 13, wherein the second sensor data comprises canopy sensor data from one or more canopy scanning sensors, the canopy sensor data comprising information about a three-dimensional structure of each of the second plants.

18. The apparatus of claim 13, wherein the second sensor data comprises data from one or more cameras that capture images of the multiple plants.

19. The apparatus of claim 13, wherein the second sensor data comprises data from (i) multiple cameras that capture stereo images of the multiple plants and (ii) distance sensors that capture distance measurements for calibrating the stereo images.

20. The apparatus of claim 13, wherein the at least one processor is further configured to:
generate a graphical user interface that includes a graphical representation of a growing area associated with the second plants; and
identify, using one or more markers in the graphical representation of the growing area, one or more locations of the at least one of the second plants.

21. The apparatus of claim 20, wherein:
each of the one or more markers is selectable by a user; and
the at least one processor is further configured, in response to a selection of a specified marker among the one or more markers, to present in the graphical user interface information associated with the second plant at a location associated with the specified marker.

22. The apparatus of claim 13, wherein the at least one interface is configured to receive the second sensor data from one or more microclimate sensors positioned on a mobile platform, the one or more microclimate sensors configured to generate microclimate sensor data based on a microclimate around individual ones of the second plants.

23. The apparatus of claim 13, wherein the at least one processor is configured to generate the predictive model using machine learning.

24. The apparatus of claim 13, wherein, to analyze at least some of the first sensor data to generate the predictive model, the at least one processor is configured to:
perform feature selection to identify attributes in the first sensor data that enhance an accuracy of the predictive model;
exclude any of the first sensor data that does not contribute to the accuracy of the predictive model or that decreases the accuracy of the predictive model; and
generate the predictive model based on the identified attributes and not based on the excluded first sensor data.

25. A non-transitory computer readable medium containing instructions that when executed cause at least one processor to:
receive first sensor data pertaining to plant-related parameters of each of one or more first plants that performed well over time;
analyze at least some of the first sensor data to generate a predictive model associated with the one or more first plants;
receive second sensor data pertaining to plant-related parameters of each of multiple second plants;
identify at least one of the second plants to receive one or more interventions by applying the predictive model to the second sensor data; and
cause the one or more interventions involving the at least one identified second plant to be performed;
wherein the instructions that when executed cause the at least one processor to identify the at least one of the second plants comprise:
instructions that when executed cause the at least one processor to identify the at least one of the second plants as having at least one of the plant-related parameters that deviates from at least one of the plant-related parameters of the one or more first plants.

26. The non-transitory computer readable medium of claim 25, wherein the instructions when executed cause the at least one processor to select the one or more interventions in order to increase a predicted future performance of the at least one identified second plant towards a performance of the one or more first plants.

27. The non-transitory computer readable medium of claim 25, wherein the one or more interventions comprise at least one of: dispersion of a bio-control agent, activation of an irrigation system, adjustment of a temperature control system, or administration of a nutrient or a pesticide.

28. The non-transitory computer readable medium of claim 25, further containing instructions that when executed cause the at least one processor to output, to a user, a notification identifying the one or more interventions involving the at least one identified second plant.

29. The non-transitory computer readable medium of claim 25, wherein the second sensor data comprises canopy sensor data from one or more canopy scanning sensors, the canopy sensor data comprising information about a three-dimensional structure of each of the second plants.

30. The non-transitory computer readable medium of claim 25, wherein the second sensor data comprises data from one or more cameras that capture images of the multiple plants.

31. The non-transitory computer readable medium of claim 25, wherein the second sensor data comprises data from (i) multiple cameras that capture stereo images of the multiple plants and (ii) distance sensors that capture distance measurements for calibrating the stereo images.

32. The non-transitory computer readable medium of claim 25, further containing instructions that when executed cause the at least one processor to:
   generate a graphical user interface that includes a graphical representation of a growing area associated with the second plants; and
   identify, using one or more markers in the graphical representation of the growing area, one or more locations of the at least one of the second plants.

33. The non-transitory computer readable medium of claim 32, wherein:
   each of the one or more markers is selectable by a user; and
   the non-transitory computer readable medium further contains instructions that when executed cause the at least one processor, in response to a selection of a specified marker among the one or more markers, to present in the graphical user interface information associated with the second plant at a location associated with the specified marker.

34. The non-transitory computer readable medium of claim 25, wherein the second sensor data comprises microclimate sensor data from one or more microclimate sensors positioned on a mobile platform, the one or more microclimate sensors configured to generate the microclimate sensor data based on a microclimate around individual ones of the second plants.

35. The non-transitory computer readable medium of claim 25, wherein the instructions when executed cause the at least one processor to generate the predictive model using machine learning.

36. The non-transitory computer readable medium of claim 25, wherein the instructions when executed cause the at least one processor to analyze at least some of the first sensor data to generate the predictive model comprise:
   instructions when executed cause the at least one processor to:
      perform feature selection to identify attributes in the first sensor data that enhance an accuracy of the predictive model;
      exclude any of the first sensor data that does not contribute to the accuracy of the predictive model or that decreases the accuracy of the predictive model; and
      generate the predictive model based on the identified attributes and not based on the excluded first sensor data.

* * * * *